US011192932B2

(12) United States Patent
Delale et al.

(10) Patent No.: US 11,192,932 B2
(45) Date of Patent: *Dec. 7, 2021

(54) HEPARIN-BINDING DOMAIN OF IGFBP-2 IN THE TREATMENT OF METABOLIC DISORDERS

(71) Applicant: Amolyt Pharma, Ecully (FR)

(72) Inventors: Thomas Delale, Charbonnieres-les-Bains (FR); Stephane Milano, Saint Nizier d'Azergues (FR); Thierry Abribat, St-Foy-les-Lyon (FR); David Clemmons, Chapel Hill, NC (US)

(73) Assignee: Amolyt Pharma, Ecully (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/420,656

(22) Filed: May 23, 2019

(65) Prior Publication Data

US 2019/0359676 A1 Nov. 28, 2019

Related U.S. Application Data

(60) Provisional application No. 62/676,087, filed on May 24, 2018.

(51) Int. Cl.
| | |
|---|---|
| C07K 14/655 | (2006.01) |
| A61P 3/10 | (2006.01) |
| A61P 3/04 | (2006.01) |
| C07K 7/64 | (2006.01) |
| C07K 14/47 | (2006.01) |
| C07K 7/52 | (2006.01) |
| A61K 47/60 | (2017.01) |
| A61K 38/17 | (2006.01) |
| A61K 38/00 | (2006.01) |

(52) U.S. Cl.
CPC ........ *C07K 14/655* (2013.01); *A61K 38/1754* (2013.01); *A61K 47/60* (2017.08); *A61P 3/04* (2018.01); *A61P 3/10* (2018.01); *C07K 7/52* (2013.01); *C07K 7/64* (2013.01); *C07K 14/4743* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 9,220,746 B2 | 12/2015 | Clemmons et al. | |
| 2003/0165996 A1 | 9/2003 | Halkier et al. | |
| 2008/0227125 A1 | 9/2008 | Argoud-Puy et al. | |
| 2012/0149634 A1* | 6/2012 | Clemmons | A61P 35/00 |
| | | | 514/4.8 |
| 2014/0100160 A1 | 4/2014 | Hwang | |
| 2015/0038435 A1* | 2/2015 | Hubalek | C07K 5/1008 |
| | | | 514/21.6 |
| 2016/0039897 A1* | 2/2016 | Clemmons | A61K 45/06 |
| | | | 514/4.8 |
| 2018/0230191 A1* | 8/2018 | Clemmons | C07K 14/4743 |
| 2019/0352358 A1 | 11/2019 | Clemmons et al. | |

FOREIGN PATENT DOCUMENTS

| | | |
|---|---|---|
| WO | WO2002024219 A1 | 3/2002 |
| WO | WO2005014635 A2 | 2/2005 |
| WO | WO2006102715 A1 | 10/2006 |
| WO | WO2008019491 A1 | 2/2008 |
| WO | WO2009059011 A2 | 5/2009 |
| WO | WO2010-096125 | 8/2010 |
| WO | WO2010141811 A2 | 12/2010 |
| WO | WO2014165137 A1 | 10/2014 |
| WO | WO2018/145006 A1 | 8/2018 |
| WO | WO-2018145006 A1 * | 8/2018 ............. A61P 19/10 |

OTHER PUBLICATIONS

Huvenne et al. "Rare Genetic Forms of Obesity: Clinical Approach and Current Treatments in 2016," Obes Facts. Jun. 2016; 9(3): 158-173 (Year: 2016).*
Chung "An Overview of Monogenic and Syndromic Obesities in Humans," Pediatr Blood Cancer. Jan. 2012; 58(1): 122-128 (Year: 2012).*
Joo "Cyclic Peptides as Therapeutic Agents and Biochemical Tools," Biomol. Ther., 2012, vol. 20(1): 19-26 (Year: 2012).*
Xi et al. "The Heparin-Binding Domains of IGFBP-2 Mediate Its Inhibitory Effect on Preadipocyte Differentiation and Fat Development in Male Mice", Endocrinology, 2013, vol. 154; No. 11, pp. 4146-4157.
Poster 0268 by Xi et al. presented at the Annual Meeting of the American Society for Bone and Mineral Research (ASBMR) in Atlanta on Sep. 16-19, 2016. A unique peptide containing the heparin binding domain of IGFBP-2 increases bone mass in ovariectomized (OVX) rats.
Wheatcroft et al. "IGF-Binding Protein-2 Protects Against the Development of Obesity and Insulin Resistance", Diabetes, 2007, vol. 56, No. 2, pp. 285-294.
DeMambro et al. "Gender-Specific Changes in Bone Turnover and Skeletal Architecture in igfbp-2-Null Mice", Endocrinology, 2008, vol. 149, No. 5, pp. 2051-2061.
Hedbacker et al. "Antidiabetic Effects of IGFBP2, a Leptin-Regulated Gene", Cell MetabOLISM, 2010, vol. 11, No. 1, pp. 11-22.

(Continued)

*Primary Examiner* — Christina Bradley
(74) *Attorney, Agent, or Firm* — Knobbe, Martens, Olson and Bear, LLP

(57) ABSTRACT

The present technology generally relates to compounds, in particular peptides comprising the heparin-binding domain (HBD) of insulin-like growth factor binding protein-2 (IGFBP-2) for the modulation of metabolic disorders. The present technology also generally relates to uses of such compounds in methods for preventing and/or treating metabolic disorders and in compositions and formulations for such uses.

16 Claims, 6 Drawing Sheets

Specification includes a Sequence Listing.

(56) References Cited

OTHER PUBLICATIONS

Xi, G. et al. "IGFBP-2 directly stimulates osteoblast differentiation", J. Bone Miner. Res., 2014, vol. 29, No. 11, pp. 2427-2438.
Kawai et al. "The heparin binding domain of IGFBP-2 has insulin-like growth factor binding-independent biologic activity in the growing skeleton", J Biol Chem., 2011, vol. 286, No. 16, pp. 14670-14680.
Arai et al. "Binding of Insulin-Like Growth Factor (IGF) I or II to IGF-Binding Protein-2 Enables It to Bind to Heparin and Extracellular Matrix", Endocrinology, Nov. 1, 1996, vol. 137, No. 11, pp. 4571-4575.
International Search report of PCT/US2018/016869; dated May 23, 2018; Blaine R. Copenheaver.
Lim et al. "Site-specific fatty acid-conjugation to prolong protein half-life in vivo", J. Control Release, Sep. 10, 2013, vol. 170, No. 2, pp. 219-225.
Joo "Cyclic Peptides as Therapeutic Agent and Biochemical Tools", Biomolecules & Therapeutics, 2012, vol. 20, No. 1, pp. 19-26.
Kawai et al., Supplemental Data The "The heparin binding domain of IGFBP-2 has IGH binding-independent biologic activity in the growing skeleton", 6 pages.
Shen et al. "Insulin-Like Growth Factor (IGF) Binding Protein 2 Functions Coordinately with Receptor Protein Tyrosine Phosphatase β and the IGF-I Receptor to Regulate IGF-I-Stimulated Signaling", Mol. Cell Biol., 2012, vol. 32, No. 20, pp. 4116-4130.
Assefa et al. "Insulin-Like Growth Factor (IGF) Binding Protein-2, Independently of IGF-1, Induces GLUT-4 Translocation and Glucose Uptake in 3T3-L1 Adipocytes", Oxidative Medicine and Cellular Longevity, vol. 2017, Article ID: 3035184, 13 pages.
Lin, et al. "Plasma IGFBP-2 levels predict clinical outcomes of patients with high-grade gliomas" Neuro-Oncology, Oct. 2009, pp. 468-476.
International Search Report of PCT/IB19/54302, dated Nov. 1, 2019, in 19 pages.
Antonetti, DA et al., Diabetic Retinopathy Seeing Beyond Glucose-Induced Microvascular bisease. Perspectives in Diabetes. Sep. 2006, vol. 55, No. 9; pp. 2401-2411;p. 2303, 1 st colurnn, 1 st paragraph—2nd column, 3rd paragraph; p. 2407 , 1 st column, 2nd paragraph—3rd paragraph; DOI: 10.23371db05-1635.
Hoybye, C et al., The growth hormone-insulin-like growth factor axis in adult patients with Prader Willi syndrome. Growth Hormone & IGF Research. Oct. 2003, vol. 13, No. 5; pp. 269-274; abstract; p. 270, 2nd column,Sth paragraph; p. 273,1st column,4th paragraph; Table 2; DOI: 1 0.1016/S1 096-6374(03)00017-0.
Xi, G. et al., The Heparin-Binding Domains of IGFBP-2 Mediate Its Inhibitory Effect on Preadipocyte Differentiation and Fat Development in Male Mice. Endocrinology. Nov. 2013, EpubAug. 27, 2013, vol. 154, No. 11.
George, Amrutha, et al. "Lean diabetes mellitus: An emerging entity in the era of obesity, World Journal of Diabetes", May 15, 2015, 6(4): 613-620.
Hussain, et al., "Lipodystrophy Syndromes", Dermatol Clin. Author Manuscript, Oct. 2008; 26(4), in 21 pages.
Owei, et al. "Insulin-sensitive and insulin-resistant obese and non-obese phenotypes: role in prediction of incident pre-diabetes in a longitudinal biracial cohort", BMJ Open Diabetes Research & Care, Jul. 20, 2017, in 10 pages.

* cited by examiner

```
                        SEQUENCE LISTING

<160> NUMBER OF SEQ ID NOS: 113

<210> SEQ ID NO 1
<211> LENGTH: 13
<212> TYPE: PRT
<213> ORGANISM: Artificial Sequence
<220> FEATURE:
<223> OTHER INFORMATION: Synthesized

<400> SEQUENCE: 1

Lys His His Leu Gly Leu Glu Glu Pro Lys Lys Leu Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthesized

<400> SEQUENCE: 2

His His Leu Gly Leu Glu Glu Pro Lys Lys Leu Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthesized

<400> SEQUENCE: 3

His Leu Gly Leu Glu Glu Pro Lys Lys Leu Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthesized

<400> SEQUENCE: 4

Leu Gly Leu Glu Glu Pro Lys Lys Leu Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthesized

<400> SEQUENCE: 5

Lys His His Leu Gly Leu Glu Glu Pro Lys Lys Leu
1               5                   10

<210> SEQ ID NO 6
<211> LENGTH: 11
<212> TYPE: PRT
<213> ORGANISM: Artificial Sequence
```

```
<220> FEATURE:
<223> OTHER INFORMATION: Synthesized

<400> SEQUENCE: 6

Lys His His Leu Gly Leu Glu Glu Pro Lys Lys
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthesized

<400> SEQUENCE: 7

His Leu Gly Leu Glu Glu Pro Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Synthesized

<400> SEQUENCE: 8

His Leu Gly Leu Glu Glu Pro
1               5

<210> SEQ ID NO 9
<211> LENGTH: 10
<212> TYPE: PRT
<213> ORGANISM: Artificial Sequence
<220> FEATURE:
<223> OTHER INFORMATION: Synthesized

<400> SEQUENCE: 9

His Leu Gly Leu Glu Glu Pro Lys Lys Leu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthesized

<400> SEQUENCE: 10

His Leu Gly Leu Glu Glu Pro Lys Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Synthesized

<400> SEQUENCE: 11

Leu Gly Leu Glu Glu Pro Lys Lys
1               5

<210> SEQ ID NO 12
<211> LENGTH: 7
<212> TYPE: PRT
<213> ORGANISM: Artificial Sequence
<220> FEATURE:
```

```
<223> OTHER INFORMATION: Synthesized

<400> SEQUENCE: 12

Gly Leu Glu Glu Pro Lys Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Synthesized

<400> SEQUENCE: 13

Leu Gly Leu Glu Glu Pro Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthesized

<400> SEQUENCE: 14

Gly Leu Glu Glu Pro Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Synthesized

<400> SEQUENCE: 15

Leu Gly Leu Glu Glu Pro
1               5

<210> SEQ ID NO 16
<211> LENGTH: 10
<212> TYPE: PRT
<213> ORGANISM: Artificial Sequence
<220> FEATURE:
<223> OTHER INFORMATION: Synthesized

<400> SEQUENCE: 16

His His Leu Gly Leu Glu Glu Pro Lys Lys
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthesized

<400> SEQUENCE: 17

Ala Leu Gly Leu Glu Glu Pro Lys Lys
1               5

<210> SEQ ID NO 18
<211> LENGTH: 9
<212> TYPE: PRT
<213> ORGANISM: Artificial Sequence
<220> FEATURE:
<223> OTHER INFORMATION: Synthesized
```

```
<400> SEQUENCE: 18

His Ala Gly Leu Glu Glu Pro Lys Lys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthesized

<400> SEQUENCE: 19

His Leu Ala Leu Glu Glu Pro Lys Lys
1               5

<210> SEQ ID NO 20
<211> LENGTH: 9
<212> TYPE: PRT
<213> ORGANISM: Artificial Sequence
<220> FEATURE:
<223> OTHER INFORMATION: Synthesized

<400> SEQUENCE: 20

His Leu Gly Ala Glu Glu Pro Lys Lys
1               5

<210> SEQ ID NO 21
<211> LENGTH: 9
<212> TYPE: PRT
<213> ORGANISM: Artificial Sequence
<220> FEATURE:
<223> OTHER INFORMATION: Synthesized

<400> SEQUENCE: 21

His Leu Gly Leu Ala Glu Pro Lys Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Synthesized

<400> SEQUENCE: 22

His Leu Gly Leu Glu Ala Pro Lys Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthesized

<400> SEQUENCE: 23

His Leu Gly Leu Glu Glu Ala Lys Lys
1               5

<210> SEQ ID NO 24
<211> LENGTH: 9
<212> TYPE: PRT
<213> ORGANISM: Artificial Sequence
<220> FEATURE:
<223> OTHER INFORMATION: Synthesized
```

```
<400> SEQUENCE: 24

His Leu Gly Leu Glu Glu Pro Ala Lys
1               5

<210> SEQ ID NO 25
<211> LENGTH: 9
<212> TYPE: PRT
<213> ORGANISM: Artificial Sequence
<220> FEATURE:
<223> OTHER INFORMATION: Synthesized

<400> SEQUENCE: 25

His Leu Gly Leu Glu Glu Pro Lys Ala
1               5

<210> SEQ ID NO 26
<211> LENGTH: 9
<212> TYPE: PRT
<213> ORGANISM: Artificial Sequence
<220> FEATURE:
<223> OTHER INFORMATION: Synthesized

<400> SEQUENCE: 26

His Leu Gly Leu Glu Arg Pro Lys Lys
1               5

<210> SEQ ID NO 27
<211> LENGTH: 9
<212> TYPE: PRT
<213> ORGANISM: Artificial Sequence
<220> FEATURE:
<223> OTHER INFORMATION: Synthesized

<400> SEQUENCE: 27

His Leu Gly Leu Glu Phe Pro Lys Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthesized

<400> SEQUENCE: 28

His Leu Gly Leu Glu Ile Pro Lys Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Synthesized

<400> SEQUENCE: 29

His Leu Gly Leu Glu Pro Pro Lys Lys
1               5

<210> SEQ ID NO 30
<211> LENGTH: 9
<212> TYPE: PRT
<213> ORGANISM: Artificial Sequence
<220> FEATURE:
<223> OTHER INFORMATION: Synthesized

<400> SEQUENCE: 30
```

```
His Leu Gly Leu Glu Ser Pro Lys Lys
1               5

<210> SEQ ID NO 31
<211> LENGTH: 9
<212> TYPE: PRT
<213> ORGANISM: Artificial Sequence
<220> FEATURE:
<223> OTHER INFORMATION: Synthesized

<400> SEQUENCE: 31

His Leu Gly Leu Glu Glu Arg Lys Lys
1               5

<210> SEQ ID NO 32
<211> LENGTH: 9
<212> TYPE: PRT
<213> ORGANISM: Artificial Sequence
<220> FEATURE:
<223> OTHER INFORMATION: Synthesized

<400> SEQUENCE: 32

His Leu Gly Leu Glu Glu Phe Lys Lys
1               5

<210> SEQ ID NO 33
<211> LENGTH: 9
<212> TYPE: PRT
<213> ORGANISM: Artificial Sequence
<220> FEATURE:
<223> OTHER INFORMATION: Synthesized

<400> SEQUENCE: 33

His Leu Gly Leu Glu Glu Leu Lys Lys
1               5

<210> SEQ ID NO 34
<211> LENGTH: 9
<212> TYPE: PRT
<213> ORGANISM: Artificial Sequence
<220> FEATURE:
<223> OTHER INFORMATION: Synthesized

<400> SEQUENCE: 34

His Leu Gly Leu Glu Glu Ser Lys Lys
1               5

<210> SEQ ID NO 35
<211> LENGTH: 9
<212> TYPE: PRT
<213> ORGANISM: Artificial Sequence
<220> FEATURE:
<223> OTHER INFORMATION: Synthesized

<400> SEQUENCE: 35

His Leu Gly Leu Glu Glu Asp Lys Lys
1               5

<210> SEQ ID NO 36
<211> LENGTH: 9
<212> TYPE: PRT
<213> ORGANISM: Artificial Sequence
<220> FEATURE:
<223> OTHER INFORMATION: Synthesized

<400> SEQUENCE: 36
```

His Leu Gly Leu Glu Glu Pro Phe Lys
1               5

<210> SEQ ID NO 37
<211> LENGTH: 9
<212> TYPE: PRT
<213> ORGANISM: Artificial Sequence
<220> FEATURE:
<223> OTHER INFORMATION: Synthesized

<400> SEQUENCE: 37

His Leu Gly Leu Glu Glu Pro Pro Lys
1               5

<210> SEQ ID NO 38
<211> LENGTH: 9
<212> TYPE: PRT
<213> ORGANISM: Artificial Sequence
<220> FEATURE:
<223> OTHER INFORMATION: Synthesized

<400> SEQUENCE: 38

His Leu Gly Leu Glu Glu Pro Ser Lys
1               5

<210> SEQ ID NO 39
<211> LENGTH: 9
<212> TYPE: PRT
<213> ORGANISM: Artificial Sequence
<220> FEATURE:
<223> OTHER INFORMATION: Synthesized

<400> SEQUENCE: 39

His Leu Gly Leu Glu Glu Pro Asp Lys
1               5

<210> SEQ ID NO 40
<211> LENGTH: 9
<212> TYPE: PRT
<213> ORGANISM: Artificial Sequence
<220> FEATURE:
<223> OTHER INFORMATION: Synthesized

<400> SEQUENCE: 40

His Leu Gly Leu Glu Glu Pro Lys Phe
1               5

<210> SEQ ID NO 41
<211> LENGTH: 9
<212> TYPE: PRT
<213> ORGANISM: Artificial Sequence
<220> FEATURE:
<223> OTHER INFORMATION: Synthesized

<400> SEQUENCE: 41

His Leu Gly Leu Glu Glu Pro Lys Ile
1               5

<210> SEQ ID NO 42
<211> LENGTH: 9
<212> TYPE: PRT
<213> ORGANISM: Artificial Sequence
<220> FEATURE:
<223> OTHER INFORMATION: Synthesized

<400> SEQUENCE: 42

His Leu Gly Leu Glu Glu Pro Lys Pro

```
1               5

<210> SEQ ID NO 43
<211> LENGTH: 9
<212> TYPE: PRT
<213> ORGANISM: Artificial Sequence
<220> FEATURE:
<223> OTHER INFORMATION: Synthesized

<400> SEQUENCE: 43

His Leu Gly Leu Glu Glu Pro Lys Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Synthesized

<400> SEQUENCE: 44

His Leu Gly Leu Glu Glu Pro Lys Asp
1               5

<210> SEQ ID NO 45
<211> LENGTH: 9
<212> TYPE: PRT
<213> ORGANISM: Artificial Sequence
<220> FEATURE:
<223> OTHER INFORMATION: Synthesized

<400> SEQUENCE: 45

His Leu Gly Leu Glu Glu Pro Ile Lys
1               5

<210> SEQ ID NO 46
<211> LENGTH: 9
<212> TYPE: PRT
<213> ORGANISM: Artificial Sequence
<220> FEATURE:
<223> OTHER INFORMATION: Synthesized

<400> SEQUENCE: 46

His Leu Gly Leu Glu Glu Pro Val Lys
1               5

<210> SEQ ID NO 47
<211> LENGTH: 9
<212> TYPE: PRT
<213> ORGANISM: Artificial Sequence
<220> FEATURE:
<223> OTHER INFORMATION: Synthesized

<400> SEQUENCE: 47

His Leu Gly Leu Glu Glu Pro Gln Lys
1               5

<210> SEQ ID NO 48
<211> LENGTH: 9
<212> TYPE: PRT
<213> ORGANISM: Artificial Sequence
<220> FEATURE:
<223> OTHER INFORMATION: Synthesized

<400> SEQUENCE: 48

His Leu Gly Leu Glu Glu Pro Thr Lys
1               5
```

```
<210> SEQ ID NO 49
<211> LENGTH: 9
<212> TYPE: PRT
<213> ORGANISM: Artificial Sequence
<220> FEATURE:
<223> OTHER INFORMATION: Synthesized

<400> SEQUENCE: 49

His Leu Gly Leu Glu Glu Pro Glu Lys
1               5

<210> SEQ ID NO 50
<211> LENGTH: 9
<212> TYPE: PRT
<213> ORGANISM: Artificial Sequence
<220> FEATURE:
<223> OTHER INFORMATION: Synthesized

<400> SEQUENCE: 50

His Leu Gly Leu Glu Glu Pro Lys His
1               5

<210> SEQ ID NO 51
<211> LENGTH: 9
<212> TYPE: PRT
<213> ORGANISM: Artificial Sequence
<220> FEATURE:
<223> OTHER INFORMATION: Synthesized

<400> SEQUENCE: 51

His Leu Gly Leu Glu Glu Pro Lys Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Synthesized

<400> SEQUENCE: 52

His Leu Gly Leu Glu Glu Pro Lys Leu
1               5

<210> SEQ ID NO 53
<211> LENGTH: 9
<212> TYPE: PRT
<213> ORGANISM: Artificial Sequence
<220> FEATURE:
<223> OTHER INFORMATION: Synthesized

<400> SEQUENCE: 53

His Leu Gly Leu Glu Glu Pro Lys Met
1               5

<210> SEQ ID NO 54
<211> LENGTH: 9
<212> TYPE: PRT
<213> ORGANISM: Artificial Sequence
<220> FEATURE:
<223> OTHER INFORMATION: Synthesized

<400> SEQUENCE: 54

His Leu Gly Leu Glu Glu Pro Lys Trp
1               5
```

<210> SEQ ID NO 55
<211> LENGTH: 9
<212> TYPE: PRT
<213> ORGANISM: Artificial Sequence
<220> FEATURE:
<223> OTHER INFORMATION: Synthesized

<400> SEQUENCE: 55

His Leu Gly Leu Glu Glu Pro Lys Val
1               5

<210> SEQ ID NO 56
<211> LENGTH: 9
<212> TYPE: PRT
<213> ORGANISM: Artificial Sequence
<220> FEATURE:
<223> OTHER INFORMATION: Synthesized

<400> SEQUENCE: 56

His Leu Gly Leu Glu Glu Pro Lys Gln
1               5

<210> SEQ ID NO 57
<211> LENGTH: 9
<212> TYPE: PRT
<213> ORGANISM: Artificial Sequence
<220> FEATURE:
<223> OTHER INFORMATION: Synthesized

<400> SEQUENCE: 57

His Leu Gly Leu Glu Glu Pro Lys Asn
1               5

<210> SEQ ID NO 58
<211> LENGTH: 9
<212> TYPE: PRT
<213> ORGANISM: Artificial Sequence
<220> FEATURE:
<223> OTHER INFORMATION: Snythesized

<400> SEQUENCE: 58

His Leu Gly Leu Glu Glu Pro Lys Tyr
1               5

<210> SEQ ID NO 59
<211> LENGTH: 9
<212> TYPE: PRT
<213> ORGANISM: Artificial Sequence
<220> FEATURE:
<223> OTHER INFORMATION: Synthesized

<400> SEQUENCE: 59

His Leu Gly Leu Glu Glu Pro Lys Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Synthesized

<400> SEQUENCE: 60

His Leu Gly Leu Glu Glu Pro Lys Glu
1               5

```
<210> SEQ ID NO 61
<211> LENGTH: 9
<212> TYPE: PRT
<213> ORGANISM: Artificial Sequence
<220> FEATURE:
<223> OTHER INFORMATION: Snythesized

<400> SEQUENCE: 61

His Leu Gly Leu Glu Glu Pro Ser Pro
1               5

<210> SEQ ID NO 62
<211> LENGTH: 9
<212> TYPE: PRT
<213> ORGANISM: Artificial Sequence
<220> FEATURE:
<223> OTHER INFORMATION: Synthesized

<400> SEQUENCE: 62

His Leu Gly Leu Glu Glu Pro Ser Ser
1               5

<210> SEQ ID NO 63
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<220> FEATURE:
<221> NAME/KEY: MOD_RES
<222> LOCATION: (1)..(1)
<223> OTHER INFORMATION: Pegylated

<400> SEQUENCE: 63

Lys His His Leu Gly Leu Glu Glu Pro Lys Lys Leu Arg
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (13)..(13)
<223> OTHER INFORMATION: Pegylated

<400> SEQUENCE: 64

Lys His His Leu Gly Leu Glu Glu Pro Lys Lys Leu Arg
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Pegylated

<400> SEQUENCE: 65

His His Leu Gly Leu Glu Glu Pro Lys Lys
1               5                   10
```

```
<210> SEQ ID NO 66
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (10)..(10)
<223> OTHER INFORMATION: Pegylated

<400> SEQUENCE: 66

His His Leu Gly Leu Glu Glu Pro Lys Lys
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Snythesized
<220> FEATURE:
<221> NAME/KEY: MOD_RES
<222> LOCATION: (1)..(1)
<223> OTHER INFORMATION: Pegylated

<400> SEQUENCE: 67

His Leu Gly Leu Glu Glu Pro Lys Lys
1               5

<210> SEQ ID NO 68
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C16:0

<400> SEQUENCE: 68

His His Leu Gly Leu Glu Glu Pro Lys Lys
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C18:0

<400> SEQUENCE: 69

His His Leu Gly Leu Glu Glu Pro Lys Lys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C20:0
```

```
<400> SEQUENCE: 70

His His Leu Gly Leu Glu Glu Pro Lys Lys
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C14:0

<400> SEQUENCE: 71

His Leu Gly Leu Glu Glu Pro Lys Lys
1               5

<210> SEQ ID NO 72
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C16:0

<400> SEQUENCE: 72

His Leu Gly Leu Glu Glu Pro Lys Lys
1               5

<210> SEQ ID NO 73
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C18:0

<400> SEQUENCE: 73

His Leu Gly Leu Glu Glu Pro Lys Lys
1               5

<210> SEQ ID NO 74
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C20:0

<400> SEQUENCE: 74

His Leu Gly Leu Glu Glu Pro Lys Lys
1               5

<210> SEQ ID NO 75
<211> LENGTH: 9
<212> TYPE: PRT
<213> ORGANISM: Artificial Sequence
```

```
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Di-acylated with C16:0

<400> SEQUENCE: 75

His Leu Gly Leu Glu Glu Pro Lys Lys
1               5

<210> SEQ ID NO 76
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (9)..(9)
<223> OTHER INFORMATION: Acylated with C16:0

<400> SEQUENCE: 76

His Leu Gly Leu Glu Glu Pro Lys Lys
1               5

<210> SEQ ID NO 77
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(9)
<223> OTHER INFORMATION: Cyclic peptide

<400> SEQUENCE: 77

His Leu Gly Leu Glu Glu Pro Lys Lys
1               5

<210> SEQ ID NO 78
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C16:0

<400> SEQUENCE: 78

Lys His His Leu Gly Leu Glu Glu Pro Lys Lys Leu Arg
1               5                   10

<210> SEQ ID NO 79
<211> LENGTH: 6
<212> TYPE: PRT
<213> ORGANISM: Artificial Sequence
<220> FEATURE:
<223> OTHER INFORMATION: Synthesized

<400> SEQUENCE: 79

Gly Leu Glu Glu Pro Leu
1               5

<210> SEQ ID NO 80
<211> LENGTH: 6
```

```
<212> TYPE: PRT
<213> ORGANISM: Artificial Sequence
<220> FEATURE:
<223> OTHER INFORMATION: Synthesized

<400> SEQUENCE: 80

Gly Leu Glu Glu Pro Arg
1               5

<210> SEQ ID NO 81
<211> LENGTH: 6
<212> TYPE: PRT
<213> ORGANISM: Artificial Sequence
<220> FEATURE:
<223> OTHER INFORMATION: Snythesized

<400> SEQUENCE: 81

Gly Leu Asp Glu Pro Lys
1               5

<210> SEQ ID NO 82
<211> LENGTH: 6
<212> TYPE: PRT
<213> ORGANISM: Artificial Sequence
<220> FEATURE:
<223> OTHER INFORMATION: Synthesized

<400> SEQUENCE: 82

Gly Leu Glu Asp Pro Lys
1               5

<210> SEQ ID NO 83
<211> LENGTH: 6
<212> TYPE: PRT
<213> ORGANISM: Artificial Sequence
<220> FEATURE:
<223> OTHER INFORMATION: Synthesized

<400> SEQUENCE: 83

Gly Gly Glu Glu Pro Lys
1               5

<210> SEQ ID NO 84
<211> LENGTH: 6
<212> TYPE: PRT
<213> ORGANISM: Artificial Sequence
<220> FEATURE:
<223> OTHER INFORMATION: Synthesized

<400> SEQUENCE: 84

Gly Val Glu Glu Pro Lys
1               5

<210> SEQ ID NO 85
<211> LENGTH: 6
<212> TYPE: PRT
<213> ORGANISM: Artificial Sequence
<220> FEATURE:
<223> OTHER INFORMATION: Synthesized

<400> SEQUENCE: 85

Gly Ile Glu Glu Pro Lys
1               5

<210> SEQ ID NO 86
<211> LENGTH: 6
<212> TYPE: PRT
```

```
<213> ORGANISM: Artificial Sequence
<220> FEATURE:
<223> OTHER INFORMATION: Synthesized

<400> SEQUENCE: 86

Val Leu Glu Glu Pro Lys
1               5

<210> SEQ ID NO 87
<211> LENGTH: 6
<212> TYPE: PRT
<213> ORGANISM: Artificial Sequence
<220> FEATURE:
<223> OTHER INFORMATION: Synthesized

<400> SEQUENCE: 87

Leu Leu Glu Glu Pro Lys
1               5

<210> SEQ ID NO 88
<211> LENGTH: 6
<212> TYPE: PRT
<213> ORGANISM: Artificial Sequence
<220> FEATURE:
<223> OTHER INFORMATION: Synthesized

<400> SEQUENCE: 88

Ile Leu Glu Glu Pro Lys
1               5

<210> SEQ ID NO 89
<211> LENGTH: 9
<212> TYPE: PRT
<213> ORGANISM: Artificial Sequence
<220> FEATURE:
<223> OTHER INFORMATION: Synthesized

<400> SEQUENCE: 89

Lys Leu Gly Leu Glu Glu Pro Lys Lys
1               5

<210> SEQ ID NO 90
<211> LENGTH: 9
<212> TYPE: PRT
<213> ORGANISM: Artificial Sequence
<220> FEATURE:
<223> OTHER INFORMATION: Synthesized

<400> SEQUENCE: 90

His Val Gly Leu Glu Glu Pro Lys Lys
1               5

<210> SEQ ID NO 91
<211> LENGTH: 9
<212> TYPE: PRT
<213> ORGANISM: Artificial Sequence
<220> FEATURE:
<223> OTHER INFORMATION: Synthesized

<400> SEQUENCE: 91

His Leu Pro Leu Glu Glu Pro Lys Lys
1               5

<210> SEQ ID NO 92
<211> LENGTH: 9
<212> TYPE: PRT
<213> ORGANISM: Artificial Sequence
```

```
<220> FEATURE:
<223> OTHER INFORMATION: Synthesized

<400> SEQUENCE: 92

His Leu Gly Ile Glu Glu Pro Lys Lys
1               5

<210> SEQ ID NO 93
<211> LENGTH: 9
<212> TYPE: PRT
<213> ORGANISM: Artificial Sequence
<220> FEATURE:
<223> OTHER INFORMATION: Synthesized

<400> SEQUENCE: 93

Asn Leu Gly Leu Glu Glu Pro Lys Lys
1               5

<210> SEQ ID NO 94
<211> LENGTH: 9
<212> TYPE: PRT
<213> ORGANISM: Artificial Sequence
<220> FEATURE:
<223> OTHER INFORMATION: Synthesized

<400> SEQUENCE: 94

His Thr Gly Leu Glu Glu Pro Lys Lys
1               5

<210> SEQ ID NO 95
<211> LENGTH: 9
<212> TYPE: PRT
<213> ORGANISM: Artificial Sequence
<220> FEATURE:
<223> OTHER INFORMATION: Synthesized

<400> SEQUENCE: 95

His Leu Lys Leu Glu Glu Pro Lys Lys
1               5

<210> SEQ ID NO 96
<211> LENGTH: 9
<212> TYPE: PRT
<213> ORGANISM: Artificial Sequence
<220> FEATURE:
<223> OTHER INFORMATION: Synthesized

<400> SEQUENCE: 96

His Leu Gly Ser Glu Glu Pro Lys Lys
1               5

<210> SEQ ID NO 97
<211> LENGTH: 9
<212> TYPE: PRT
<213> ORGANISM: Artificial Sequence
<220> FEATURE:
<223> OTHER INFORMATION: Synthesized

<400> SEQUENCE: 97

His Leu Gly Leu Glu Glu Pro Tyr Lys
1               5

<210> SEQ ID NO 98
<211> LENGTH: 9
<212> TYPE: PRT
<213> ORGANISM: Artificial Sequence
<220> FEATURE:
```

<223> OTHER INFORMATION: Synthesized

<400> SEQUENCE: 98

His Leu Gly Leu Glu Glu Pro Gln Lys
1               5

<210> SEQ ID NO 99
<211> LENGTH: 9
<212> TYPE: PRT
<213> ORGANISM: Artificial Sequence
<220> FEATURE:
<223> OTHER INFORMATION: Synthesized

<400> SEQUENCE: 99

His Leu Gly Leu Glu Glu Pro Asn Lys
1               5

<210> SEQ ID NO 100
<211> LENGTH: 9
<212> TYPE: PRT
<213> ORGANISM: Artificial Sequence
<220> FEATURE:
<223> OTHER INFORMATION: Synthesized

<400> SEQUENCE: 100

His Leu Gly Leu Glu Glu Pro Ser Phe
1               5

<210> SEQ ID NO 101
<211> LENGTH: 9
<212> TYPE: PRT
<213> ORGANISM: Artificial Sequence
<220> FEATURE:
<223> OTHER INFORMATION: Synthesized

<400> SEQUENCE: 101

His Leu Gly Leu Glu Glu Pro Ser Val
1               5

<210> SEQ ID NO 102
<211> LENGTH: 9
<212> TYPE: PRT
<213> ORGANISM: Artificial Sequence
<220> FEATURE:
<223> OTHER INFORMATION: Synthesized

<400> SEQUENCE: 102

His Leu Gly Leu Glu Glu Pro Leu Met
1               5

<210> SEQ ID NO 103
<211> LENGTH: 9
<212> TYPE: PRT
<213> ORGANISM: Artificial Sequence
<220> FEATURE:
<223> OTHER INFORMATION: Synthesized

<400> SEQUENCE: 103

His Leu Gly Leu Glu Glu Pro Leu Tyr
1               5

<210> SEQ ID NO 104
<211> LENGTH: 9
<212> TYPE: PRT
<213> ORGANISM: Artificial Sequence
<220> FEATURE:
<223> OTHER INFORMATION: Synthesized

```
<400> SEQUENCE: 104

His Leu Gly Leu Glu Glu Pro Leu Asn
1               5

<210> SEQ ID NO 105
<211> LENGTH: 9
<212> TYPE: PRT
<213> ORGANISM: Artificial Sequence
<220> FEATURE:
<223> OTHER INFORMATION: Synthesized

<400> SEQUENCE: 105

His Leu Gly Leu Glu Glu Pro Leu Gln
1               5

<210> SEQ ID NO 106
<211> LENGTH: 9
<212> TYPE: PRT
<213> ORGANISM: Artificial Sequence
<220> FEATURE:
<223> OTHER INFORMATION: Synthesized

<400> SEQUENCE: 106

His Leu Gly Leu Glu Glu Pro Phe Val
1               5

<210> SEQ ID NO 107
<211> LENGTH: 9
<212> TYPE: PRT
<213> ORGANISM: Artificial Sequence
<220> FEATURE:
<223> OTHER INFORMATION: Synthesized

<400> SEQUENCE: 107

His Leu Gly Leu Glu Glu Pro Phe Gln
1               5

<210> SEQ ID NO 108
<211> LENGTH: 9
<212> TYPE: PRT
<213> ORGANISM: Artificial Sequence
<220> FEATURE:
<223> OTHER INFORMATION: Synthesized

<400> SEQUENCE: 108

His Leu Gly Leu Glu Glu Pro Phe Asn
1               5

<210> SEQ ID NO 109
<211> LENGTH: 9
<212> TYPE: PRT
<213> ORGANISM: Artificial Sequence
<220> FEATURE:
<223> OTHER INFORMATION: Synthesized

<400> SEQUENCE: 109

His Leu Gly Leu Glu Glu Pro Val Met
1               5

<210> SEQ ID NO 110
<211> LENGTH: 9
<212> TYPE: PRT
<213> ORGANISM: Artificial Sequence
<220> FEATURE:
<223> OTHER INFORMATION: Synthesized
```

```
<400> SEQUENCE: 110

His Leu Gly Leu Glu Glu Pro Val Asn
1               5

<210> SEQ ID NO 111
<211> LENGTH: 9
<212> TYPE: PRT
<213> ORGANISM: Artificial Sequence
<220> FEATURE:
<223> OTHER INFORMATION: Synthesized

<400> SEQUENCE: 111

His Leu Gly Leu Glu Glu Pro Met Lys
1               5

<210> SEQ ID NO 112
<211> LENGTH: 8
<212> TYPE: PRT
<213> ORGANISM: Artificial Sequence
<220> FEATURE:
<223> OTHER INFORMATION: Synthesized

<400> SEQUENCE: 112

His Leu Gly Leu Glu Glu Pro Arg
1               5

<210> SEQ ID NO 113
<211> LENGTH: 8
<212> TYPE: PRT
<213> ORGANISM: Artificial Sequence
<220> FEATURE:
<223> OTHER INFORMATION: Synthesized

<400> SEQUENCE: 113

His Leu Gly Leu Glu Glu Pro His
1               5
```

HEPARIN-BINDING DOMAIN OF IGFBP-2 IN THE TREATMENT OF METABOLIC DISORDERS

CROSS-REFERENCE TO RELATED APPLICATION

The present application claims priority to and benefit from U.S. Provisional Patent Application 62/676,087, filed on May 24, 2018, the disclosure of which is incorporated herein by reference in its entirety.

FIELD OF TECHNOLOGY

The present technology generally relates to compounds, in particular peptides comprising the heparin-binding domain (HBD) of insulin-like growth factor binding protein-2 (IGFBP-2) for the prevention and/or the treatment of metabolic disorders. The present technology also generally relates to uses of such compounds in methods for preventing or treating metabolic disorders and to compositions and formulations for such uses.

BACKGROUND INFORMATION

Insulin-like growth factor binding protein-2 (IGFBP-2) is a 36,000 Dalton protein that is a member of the IGFBP family. There are six (6) forms of high affinity IGF binding proteins. In addition to binding the insulin-like growth factors I and II and acting as transport proteins, notably in blood, these proteins have been shown to have some direct tissue effects that are independent of their ability to bind to IGFs.

IGFBP-2 is the second most abundant binding protein in serum. It circulates in concentrations in humans that vary between 100-600 ng/ml in healthy subjects. Protein concentrations are high during fetal life and at birth and fall progressively during childhood and adolescence. There is approximately 25% increase that occurs between 60-80 years of age. Serum concentrations of IGFBP-2 are regulated by hormones and nutrients. Fasting causes a significant increase in IGFBP-2 and feeding (particularly feeding protein) restores concentrations to normal.

In addition to its role as a carrier protein for Insulin-like growth factors, IGFBP-2 regulates bone mass, fat metabolism and glucose metabolism. IGFBP-2 knockout mice (IGFBP-2$^{-/-}$) have reduced bone mass and increased fat mass (DeMambro, Endocrinology, 2008). In contrast, overexpression of IGFBP-2 in mice led to reduced susceptibility to diet-induced obesity and improved insulin sensitivity (Wheatcroft, Diabetes, 2007; Hedbacker, Cell Metab, 2010). In vitro, IGFBP-2 directly stimulates murine and human osteoblast differentiation (Xi, JBMR, 2014) and in contrast inhibits preadipocyte differentiation (Wheatcroft, Diabetes, 2007). As for other IGFBPs, the N-terminal region of IGFBP-2 contains an IGF-I binding site, whereas the C-terminal region facilitates IGF-I binding and accounts for its ability to bind to extracellular matrix.

IGFBP-2 also comprises two heparin binding domains (HBD) that confer IGF-binding independent functions. HBD1 is a unique HBD that is located in the linker region whereas HBD2 is located in the C-terminal region. While both HBD1 and HBD2 account for the ability of IGFBP-2 to inhibit adipogenesis (Xi, Endocrinology, 2013), only HBD1 mediates properties on bone mass acquisition and on osteoblast differentiation (Kawai, J B C, 2011; Xi, JBMR, 2014).

Prior studies have disclosed peptides including the HBD. For example, WO 2005/014635 discloses Cardiovascular disorder Plasma Polypeptides (CPPs) sharing amino acid sequence similarities with HBD1 and suggests a potential diagnostic function for such CPPs. U.S. Pat. No. 9,220,746 discloses HBD1 peptides which conserve the osteoblastogenesis activity of IGFBP-2 and proposes a role for these peptides in the treatment of bone-related conditions. Recently, WO 2018/145006 has proposed various fragments of HBD which induce bone formation in vivo.

To date, the experimental data available has shown that the biological effects of IGFBP-2, namely the stimulation of osteoblast differentiation and inhibition of adipocyte differentiation, are mediated, at least in part, by the HBDs of the molecule (Xi, 2013; Kawai, 2013). These properties are shared by various peptide fragments and analogs of HBD that have been derived and described in U.S. Pat. No. 9,220,746 and in WO 2018/145006. Since osteoblasts and adipocytes both originate from mesenchymal stem cells (MSCs), this suggests that the HBDs of IGBP-2 favour MSCs differentiation into osteoblasts over differentiation into adipocytes.

Another reported biological role of IGFBP-2 is on glucose control. IGFBP-2 overexpression results in improved glucose control in various animal models of leptin deficiency and other models of obesity and diabetes (Weathcroft, 2007; Hedbacker, Cell Metab, 2010). This effect appears to be due, at least in part, to increased insulin sensitivity (Hedbacker, Cell Metab, 2010). In addition, IGFBP-2 was also shown to increase glucose uptake by adipocytes and muscle cells in vitro (Assefa, 2018; Yau, 2013), and to do so through signaling pathways utilized by both insulin and insulin-like growth factor-1 (IGF1), as well as through insulin and IGF1-independent mechanisms. Interestingly, IGFBP-2 gene expression is stimulated by leptin, and IGFBP-2 has been suggested to be a mediator of the metabolic effects of leptin (Hedbacker, 2010).

Although the biology of IGFBP-2 on glucose control has been documented, it remains unknown whether the HBD domains are involved or not in these biological effects. In one publication where HBD1 and HBD2 were shown to decrease body weight and fat accumulation in mice, HBD1 and HBD2 were shown to have no effect on glucose tolerance, thereby suggesting an absence of involvement of HBDs on glucose metabolism (Xi, 2013).

It would thus be of great interest to have therapeutic peptides with the potential to modulate glucose metabolism such as, for example, to improve glucose control in subjects.

SUMMARY OF DISCLOSED TECHNOLOGY

According to various aspects, the present technology relates to a method for modulating a metabolic disorder in a subject, the method comprising: administering to the subject a therapeutically effective amount of a peptide consisting of: i) a heparin binding domain (HBD) as set forth in SEQ ID NO: 1 or an analog thereof; ii) a fragment of the peptide set forth in i); or iii) a pharmaceutically acceptable salt of any one of the peptide as set forth in i) and ii).

According to various aspects, the present technology relates to an isolated peptide consisting of: i) a heparin binding domain (HBD) as set forth in SEQ ID NO: 1 or an analog thereof; ii) a fragment of the peptide set forth in i); or iii) a pharmaceutically acceptable salt of any one of the peptide as set forth in i) and ii), for its use in the modulation of a metabolic disorder in a subject having a metabolic disorder.

According to various aspects, the present technology relates to a kit comprising: a) a pharmaceutical composition comprising: a therapeutically effective amount of a peptide consisting of: i) a heparin binding domain (HBD) as set forth in SEQ ID NO: 1 or an analog thereof; ii) a fragment of the peptide set forth in i); or iii) a pharmaceutically acceptable salt of any one of the peptide as set forth in i) and ii); and one or more pharmaceutically acceptable carriers; and b) one or more containers for said pharmaceutical composition; and c) instructions for the use thereof in modulating a metabolic disorder.

According to various aspects, the present technology relates to a method for improving glucose control in a subject, the method comprising: administering to the subject a therapeutically effective amount of a peptide consisting of: i) a heparin binding domain (HBD) as set forth in SEQ ID NO: 1 or an analog thereof; ii) a fragment of the peptide set forth in i); or iii) a pharmaceutically acceptable salt of any one of the peptide as set forth in i) and ii).

According to various aspects, the present technology relates to an isolated peptide consisting of: i) a heparin binding domain (HBD) as set forth in SEQ ID NO: 1 or an analog thereof; ii) a fragment of the peptide set forth in i); or iii) a pharmaceutically acceptable salt of any one of the peptide as set forth in i) and ii), for its use in improving glucose control in a subject.

According to various aspects, the present technology relates to a method for improving insulin sensitivity in a subject, the method comprising: administering to the subject a therapeutically effective amount of a peptide consisting of: i) a heparin binding domain (HBD) as set forth in SEQ ID NO: 1 or an analog thereof; ii) a fragment of the peptide set forth in i); or iii) a pharmaceutically acceptable salt or any one of the peptide as set forth in i) and ii).

According to various aspects, the present technology relates to a method for restoring glucose homeostasis in a subject, the method comprising: administering to the subject a therapeutically effective amount of a peptide consisting of: i) a heparin binding domain (HBD) as set forth in SEQ ID NO: 1 or an analog thereof; ii) a fragment of the peptide set forth in i); or iii) a pharmaceutically acceptable salt or any one of the peptide as set forth in i) and ii). In some instances, the method for restoring glucose homeostasis is achieved independently of insulin and insulin-like growth factor-1 (IGF1).

According to various aspects, the present technology relates to an isolated peptide consisting of: i) a heparin binding domain (HBD) as set forth in SEQ ID NO: 1 or an analog thereof; ii) a fragment of the peptide set forth in i); or iii) a pharmaceutically acceptable salt of any one of the peptide as set forth in i) and ii), for its use in improving insulin sensitivity in a subject.

Other aspects and features of the present technology will become apparent to those ordinarily skilled in the art upon review of the following description of specific embodiments in conjunction with the accompanying drawings.

BRIEF DESCRIPTION OF DRAWINGS

All features of embodiments which are described in this disclosure are not mutually exclusive and can be combined with one another. For example, elements of one embodiment can be utilized in the other embodiments without further mention. A detailed description of specific embodiments is provided herein below with reference to the accompanying drawings in which:

FIG. 2A: 3-hour intraperitoneal glucose tolerance test profiles after 28 days of acylated HBD1 (3-11) fragment treatment. (n=5-8 in each group; p value <0.0001 at both doses vs VHL), Two-way ANOVA with multiple comparison, **p<0.0001; FIG. 2B: fasting blood glucose levels (average value within 10 min prior to IPGTT) after 28 days of acylated HBD1 (3-11) fragment treatment. (n=5-8 in each group; p value <0.005 at the 3 mg/kg dose vs VHL), Unpaired two-tailed t-test vs VHL, *p<0.005; FIG. 2C: Areas under the curve of the 3-hour intraperitoneal glucose tolerance test profiles after 28 days of acylated HBD1 (3-11) fragment treatment. (n=5-8 in each group), Unpaired two-tailed t-test vs VHL,*p<0.05, ****p<0.0001.

FIG. 3A: 16-hour mean blood glucose levels before (Day −1) and after 27 days of acylated HBD1 (3-11) fragment treatment. (n=5-8 in each group; p value <0.001 at the 3 mg/kg dose vs VHL); FIG. 3B: Change from baseline in 16-hour mean blood glucose level after 27 days of acylated HBD1 (3-11) fragment treatment. (n=5-8 in each group; p value <0.01 at the 3 mg/kg dose vs VHL).

DETAILED DESCRIPTION OF TECHNOLOGY

Figure 1:
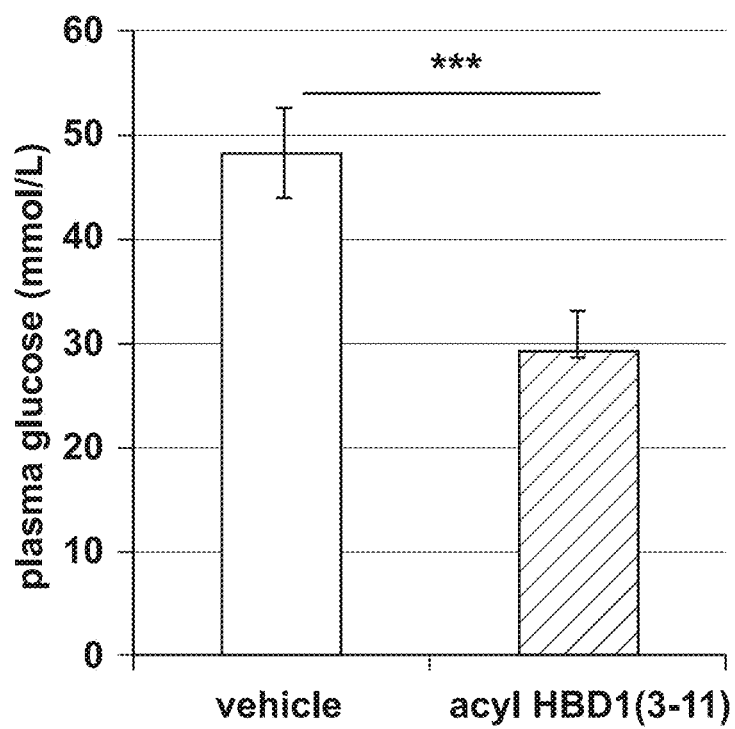
FIG. 1 is a graph showing that a HBD1 fragment according to one embodiment of the present technology improves glucose intolerance in ob/ob mice, a mouse model with leptin deficiency leading to insulin resistance, after two weeks of acylated HBD1 (3-11) fragment treatment. Data shown are blood glucose levels (Mean±SEM) 45 min after intraperitoneal glucose tolerance test (IPGTT). (n=5 in each group; ***: p value <0.001).

This present description of the technology is not intended to be a detailed catalog of all the different ways in which the present technology may be implemented, or all the features that may be added to the present technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which does not depart from the present technology. Hence, the following specification is intended to illustrate some particular embodiments of the present technology, and not to exhaustively specify all permutations, combinations and variations thereof. Unless defined otherwise, all technical and scientific terms used herein have the same meaning as commonly understood by one of skill in the art to which the present technology belongs.

As used herein, the singular form "a," "an" and "the" include plural referents unless the context clearly dictates otherwise.

The recitation herein of numerical ranges by endpoints is intended to include all numbers subsumed within that range (e.g., a recitation of 1 to 5 includes 1, 1.5, 2, 2.75, 3, 3.80, 4, 4.32, and 5).

The term "about" is used herein explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. For example, the term "about" in the context of a given value or range refers to a value or range that is within 20%, preferably within 15%, more preferably within 10%, more preferably within 9%, more preferably within 8%, more preferably within 7%, more preferably within 6%, and more preferably within 5% of the given value or range.

The expression "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The present disclosure stems from the work performed by the present discoverers on peptide fragments of IGFBP-2, in particular on peptide fragments of the heparin binding domain (HBD) of IGFBP-2, and on their study of how these peptide fragments can be used in methods of modulating metabolic disorders in a subject, such as in methods of preventing and/or treatment metabolic disorders. In particular, the discoverers have found that the peptide fragments of the heparin binding domain 1 (HBD1) of IGFBP-2 can be used to, inter alia, modulate glucose metabolism in a subject by demonstrating that these peptides improve the overall glucose intolerance in animal models resistant to insulin.

A. Compounds, Peptides, Fragments and Analogs Thereof

As used herein, the expression and term "heparin binding domain" and "HBD" refer to the heparin binding domain of IGFBP-2, whereas the term "HBD2" refers to the heparin binding domain 2 of IGFBP-2. HBD1 is intended to refer to a peptide having the amino acid sequence as set forth in SEQ ID NO: 1, namely: $^1$-KHHLGLEEPKKLR-$^{13}$, wherein "$^1$" refers to amino acid residue at the 5'-end or at the N-Terminal of this HBD1 peptide and "$^{13}$" refers to amino acid residue at the 3'-end or at the C-Terminal of this HBD1 peptide. Accordingly, the amino acids of HBD1 occupy the following positions:

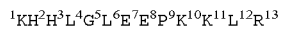

$^1$K$^2$H$^3$H$^4$L$^5$G$^6$L$^7$E$^8$E$^9$P$^{10}$K$^{11}$K$^{12}$L$^{13}$R

Well recognized abbreviations in the art will be used to describe amino acids, including levorotatory amino acids (L-amino acids or L or L-form) and dextrorotary amino acids (D-amino acids or D or D-form), Alanine (Ala or A), Arginine (Arg or R), Asparagine (Asn or N), Aspartic acid (Asp or D), Cysteine (Cys or C), Glutamic acid (Glu or E), Glutamine (Gln or Q), Glycine (Gly or G), Histidine (His or H), Isoleucine (Ile or I), Leucine (Leu or L), Lysine (Lys or K), Methionine (Met or M), Phenylalanine (Phe or F), Proline (Pro or P), Serine (Ser or S), Threonine (Thr or T), Tryptophan (Trp or W), Tyrosine (Tyr or Y) and Valine (Val or V). An L-amino acid residue within the native peptide sequence may be altered to any one of the 20 L-amino acids commonly found in proteins or any one of the corresponding D-amino acids, rare amino acids, such as, but not limited to, 4-hydroxyproline or hydroxylysine, or a non-protein amino acid, such as P-alanine or homoserine. Unless otherwise indicated, an amino acid named herein refers to the L-form.

Naturally-occurring variations of the peptides defined herein are those that may comprise substitutions, additions or deletions of one or more amino acids which result due to discrete changes in the nucleotide sequence of the encoding gene or alleles thereof or which result due to alternative splicing of the transcribed RNA. It is understood that these changes do not substantially affect the properties, pharmacological and biological characteristics of the peptide variants.

The peptides of the present disclosure may be in the form of salts. Particularly the acidic functions of the molecule may be replaced by a salt derivative thereof such as, but not limited to, a trifluoroacetate salt.

By "peptide", "polypeptide" or "protein" is meant any chain of amino acids, regardless of length or post-translational modification (e.g., glycosylation or phosphorylation), or chemical modification, or those containing unnatural or unusual amino acids such as D-Tyr, ornithine, amino-adipic acid.

In some embodiments, the peptide of the present disclosure comprises a fragment of HBD1. In some embodiments, the peptide is 13 amino acids in length. In some embodiments, the peptide is 12 amino acids in length. In some embodiments, the peptide is 11 amino acids in length. In some embodiments, the peptide is 10 amino acids in length. In some embodiments, the peptide is 9 amino acids in length.

HBD1 is 11 amino acids in length. In some embodiments, the fragment of HBD1 is 10 amino acids in length. In some embodiments, the fragment of HBD1 is 9 amino acids in length. In some other embodiments, the fragment of HBD1 is 8 amino acids in length. In some other embodiments, the fragment of HBD1 is 7 amino acids in length. In some other embodiments, the fragment of HBD1 is 6 amino acids in length. In some other embodiments, the fragment of HBD1 is 5 amino acids in length. In some other embodiments, the fragment of HBD1 is 4 amino acids in length.

In one embodiment, the present disclosure provides peptides having the amino acid sequences depicted in Table 1. HBD1 (1-13) represents the full-length HBD1. The remaining peptides presented in Table 1 are fragments of HBD1 (1-13), wherein amino acid residues at the N-terminal or at the C-terminal or at both the N-terminal and the C-terminal are absent.

TABLE 1

Examples of HBD1 peptides

| SEQ ID NOs | Fragment Surname | Amino Acid Sequence | Number of Amino acid residues |
|---|---|---|---|
| SEQ ID NO: 1 | HBD1 (1-13) | $^1$-KHHLGLEEPKKLR-$^{13}$ | 13 |
| SEQ ID NO: 2 | HBD1 (2-13) | $^1$-_HHLGLEEPKKLR-$^{13}$ | 12 |
| SEQ ID NO: 3 | HBD1 (3-13) | $^1$-__HLGLEEPKKLR-$^{13}$ | 11 |
| SEQ ID NO: 4 | HBD1 (4-13) | $^1$-___LGLEEPKKLR-$^{13}$ | 10 |
| SEQ ID NO: 5 | HBD1 (1-12) | $^1$-KHHLGLEEPKKL_-$^{13}$ | 12 |
| SEQ ID NO: 6 | HBD1 (1-11) | $^1$-KHHLGLEEPKK__-$^{13}$ | 11 |
| SEQ ID NO: 7 | HBD1 (3-10) | $^1$-__HLGLEEPK___-$^{13}$ | 8 |
| SEQ ID NO: 8 | HBD1 (3-9) | $^1$-__HLGLEEP____-$^{13}$ | 7 |
| SEQ ID NO: 9 | HBD1 (3-12) | $^1$-__HLGLEEPKKL_-$^{13}$ | 10 |
| SEQ ID NO: 10 | HBD1 (3-11) | $^1$-__HLGLEEPKK__-$^{13}$ | 9 |
| SEQ ID NO: 11 | HBD1 (4-11) | $^1$-___LGLEEPKK__-$^{13}$ | 8 |
| SEQ ID NO: 12 | HBD1 (5-11) | $^1$-____GLEEPKK__-$^{13}$ | 7 |
| SEQ ID NO: 13 | HBD1 (4-10) | $^1$-___LGLEEPK___-$^{13}$ | 7 |
| SEQ ID NO: 14 | HBD1 (5-10) | $^1$-____GLEEPK___-$^{13}$ | 6 |
| SEQ ID NO: 15 | HBD1 (4-9) | $^1$-___LGLEEP____-$^{13}$ | 6 |
| SEQ ID NO: 16 | HBD1 (2-11) | $^1$-_HHLGLEEPKK__-$^{13}$ | 10 |
| SEQ ID NO: 77 | HBD1 (3-11) cyclic | $^{cyclic1}$-HLGLEEPKK-$^{13cyclic}$ | 9 |

In some other embodiments, the peptide is 8 amino acids in length. In some other embodiments, the peptide is 7 amino acids in length. In some other embodiments, the peptide is 6 amino acids in length. In some embodiments, the peptide is 5 amino acids in length. In some embodiments, the peptide is 4 amino acids in length.

As used herein, the term and expression "fragment" or "fragment thereof" refer to an amino acid fragment of a peptide such as IGFBP-2 or of the HBD of IGFBP-2 or of the HBD1 of IGFBP-2. Fragments of HBD1 are shorter than 13 amino acid residues. Fragments of HBD1 may therefore be 12, 11, 10, 9, 8, 7, 6, 5 or 4 amino acid residues in length. In some embodiments, the fragment of HBD1 is 12 amino acids in length. In some embodiments, the fragment of In some embodiments, the peptides of the present disclosure are "purified", "isolated" or "substantially pure". The peptides are "purified", "isolated" or "substantially pure" when they are separated from the components that naturally accompany them. Typically, a compound is substantially pure when it is at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%, by weight, of the total material in a sample. Techniques for purifying or isolating peptides are commonly known and used in the art and will be known to those of skill in the art.

In some other embodiments, certain peptides according to the present disclosure may also be in cyclized form, such that the N- or C-termini are linked head-to-tail either directly, or through the insertion of a linker moiety, such moiety itself generally comprises one or more amino acid residues as required to join the backbone in such a manner as to avoid altering the three-dimensional structure of the peptide with respect to the non-cyclized form. Such peptide derivatives may have improved stability and bioavailability relative to the non-cyclized peptides.

Methods for cyclizing peptides are well known in the art. Cyclisation may be accomplished by disulfide bond formation between two side chain functional groups, amide or ester bond formation between one side chain functional group and the backbone α-amino or carboxyl function, amide or ester bond formation between two side chain functional groups, or amide bond formation between the backbone alpha-amino and carboxyl functions. These cyclisation reactions have been traditionally carried out at high dilution in solution. Cyclisation is commonly accomplished while the peptide is attached to the resin. One of the most common ways of synthesizing cyclic peptides on a solid support is by attaching the side chain of an amino acid to the resin. Using appropriate protection strategies, the C- and N-termini can be selectively deprotected and cyclized on the resin after chain assembly. This strategy is widely used, and is compatible with either tert-butyloxycarbonyl (Boc) or 9-fluorenylmethoxycarbonyl (Fmoc) protocols. However, it is restricted to peptides that contain appropriate side chain functionality to attach to the solid support. A number of approaches may be used to achieve efficient synthesis of cyclic peptides. One procedure for synthesizing cyclic peptides is based on cyclisation with simultaneous cleavage from the resin. After an appropriate peptide sequence is assembled by solid phase synthesis on the resin or a linear sequence is appended to resin, the deprotected amino group can react with its anchoring active linkage to produce protected cyclic peptides. In general, a final deprotection step is required to yield the target cyclic peptide. The procedures for synthesizing cyclic peptides are well known in the art.

In other embodiments, the present disclosure provides analogs of the peptides defined herein. As used herein, the term "analog" refers to a peptide that has the physiological activity of the parent compound thereof, and that includes one or more (e.g., two, three, four, five or six or more) amino acids different from the amino acid sequence of a naturally occurring parent peptide. Such an analog preferably has at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 07%, at least about 98% or at least about 99% of the physiological activity of the parent peptide.

In some other embodiments, the analogs may be as physiologically active as the parent (i.e., has 100% of the physiological activity of the parent peptide) or may be more than about 100%, more than about 110%, more than about 120%, more than about 130%, more than about 140%, more than about 150%, more than about 160%, more than about 170%, more than about 180%, more than about 190%, more than about 200%, or more than about 300% physiologically active than the parent peptide.

In some other embodiments, the analogs may be less physiologically active than the parent (e.g., 95% of the physiological activity of the parent peptide) but may still present a level of activity that is relevant and/or desirable for some therapeutic applications.

Such different amino acids may be additions, substitutions, deletions, or combinations thereof, including addition of non-natural side-chain groups and backbone links. Modifications of peptides to produce analogs thereof are known. See, e.g., U.S. Pat. Nos. 7,323,543; 7,482,171; 7,459,152; and 7,393,919, which are all incorporated herein by reference. For examples, analogs of peptides comprising HBD1 or analogs of fragments of HBD1 refer to either: i) structural analogs; ii) functional analogs; or iii) structural and functional analogs of HBD1 which are, inter alia, capable of replacing HBD1 in modulating glucose metabolism, such as for example, in preventing and/or treating metabolic disorders associated with impaired glucose metabolism and/or impaired insulin metabolism.

Analogs of the peptides of the present disclosure that have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98% or at least 99% sequence homology with the amino acid sequences described herein over its full length, and sharing at least one of the metabolic effects or biological activity of HBD1. A person skilled in the art would readily identify an analog sequence of HBD1 or an analog sequence of a fragment of HBD1. For example, analogs of HBD1 include, but are not limited to, peptides having the amino acid sequence as forth in SEQ ID NO: 1 (KHHLGLEEPKKLR), wherein the K or the H at position 1, 2 or 3 is substituted with R or K, the L at position 4 or 6 is substituted with I or V, the K at position 10 or 11 is substituted with H or R, the L at position 12 is substituted with I or V and/or the R at position 13 is substituted with K or H.

Analogs of HBD1 or analogs of fragment of HBD1 are, for example, analogs obtained by alanine scans or by amino acid substitutions. In some instances, analogs of HBD1 or analogs of fragments thereof may comprise a non-naturally encoded amino acid, wherein the non-naturally encoding amino acid refers to an amino acid that is not one of the common amino acids or pyrrolysine or selenocysteine, or an amino acid that occur by modification (e.g. post-translational modification) of naturally encoded amino acid (including, but not limited to, the 20 common amino acids or pyrrolysine and selenocysteine) but are not themselves incorporated into a growing polypeptide chain by the translation complex. Examples of such non-naturally-occurring amino acids include, but are not limited to, N-acetylglucosaminyl-L-serine, N-acetylglucosaminyl-L-threonine and O-phosphotyrosine. Table 2 presents examples of analogs of HBD1 (3-11) with alanine substitutions at different amino acid positions.

TABLE 2

HBD1 (3-11) fragment with Alanine substitutions at various positions

| SEQ ID NOs | Amino Acid Sequence |
|---|---|
| SEQ ID NO: 17 | ALGLEEPKK |
| SEQ ID NO: 18 | HAGLEEPKK |
| SEQ ID NO: 19 | HLALEEPKK |
| SEQ ID NO: 20 | HLGAEEPKK |

TABLE 2-continued

HBD1 (3-11) fragment with Alanine substitutions at various positions

| SEQ ID NOs | Amino Acid Sequence |
|---|---|
| SEQ ID NO: 21 | HLGLAEPKK |
| SEQ ID NO: 22 | HLGLEAPKK |
| SEQ ID NO: 23 | HLGLEEAKK |
| SEQ ID NO: 24 | HLGLEEPAK |
| SEQ ID NO: 25 | HLGLEEPKA |

Table 3 presents other examples of analogs of HBD1 fragments comprising amino acid substitutions at different amino acid positions of HBD1 (3-11).

TABLE 3

Analogs of HBD1 (3-11) fragment with amino acid substitutions at various positions

| SEQ ID NOs | Amino Acid Sequence |
|---|---|
| SEQ ID NO: 26 | HLGLERPKK |
| SEQ ID NO: 27 | HLGLEFPKK |
| SEQ ID NO: 28 | HLGLEIPKK |
| SEQ ID NO: 29 | HLGLEPPKK |
| SEQ ID NO: 30 | HLGLESPKK |
| SEQ ID NO: 31 | HLGLEERKK |
| SEQ ID NO: 32 | HLGLEEFKK |
| SEQ ID NO: 33 | HLGLEELKK |
| SEQ ID NO: 34 | HLGLEESKK |
| SEQ ID NO: 35 | HLGLEEDKK |
| SEQ ID NO: 36 | HLGLEEPFK |
| SEQ ID NO: 37 | HLGLEEPPK |
| SEQ ID NO: 38 | HLGLEEPSK |
| SEQ ID NO: 39 | HLGLEEPDK |
| SEQ ID NO: 40 | HLGLEEPKF |
| SEQ ID NO: 41 | HLGLEEPKI |
| SEQ ID NO: 42 | HLGLEEPKP |
| SEQ ID NO: 43 | HLGLEEPKS |
| SEQ ID NO: 44 | HLGLEEPKD |
| SEQ ID NO: 45 | HLGLEEPIK |
| SEQ ID NO: 46 | HLGLEEPVK |
| SEQ ID NO: 47 | HLGLEEPQK |
| SEQ ID NO: 48 | HLGLEEPTK |
| SEQ ID NO: 49 | HLGLEEPEK |
| SEQ ID NO: 50 | HLGLEEPKH |
| SEQ ID NO: 51 | HLGLEEPKR |
| SEQ ID NO: 52 | HLGLEEPKL |
| SEQ ID NO: 53 | HLGLEEPKM |
| SEQ ID NO: 54 | HLGLEEPKW |
| SEQ ID NO: 55 | HLGLEEPKV |
| SEQ ID NO: 56 | HLGLEEPKQ |
| SEQ ID NO: 57 | HLGLEEPKN |
| SEQ ID NO: 58 | HLGLEEPKY |
| SEQ ID NO: 59 | HLGLEEPKT |
| SEQ ID NO: 60 | HLGLEEPKE |
| SEQ ID NO: 61 | HLGLEEPSP |
| SEQ ID NO: 62 | HLGLEEPSS |
| SEQ ID NO: 89 | KLGLEEPKK |
| SEQ ID NO: 90 | HVGLEEPKK |
| SEQ ID NO: 91 | HLPLEEPKK |
| SEQ ID NO: 92 | HLGIEEPKK |
| SEQ ID NO: 93 | NLGLEEPKK |
| SEQ ID NO: 94 | HTGLEEPKK |
| SEQ ID NO: 95 | HLKLEEPKK |
| SEQ ID NO: 96 | HLGSEEPKK |
| SEQ ID NO: 97 | HLGLEEPYK |
| SEQ ID NO: 98 | HLGLEEPQK |
| SEQ ID NO: 99 | HLGLEEPNK |
| SEQ ID NO: 100 | HLGLEEPSF |
| SEQ ID NO: 101 | HLGLEEPSV |
| SEQ ID NO: 102 | HLGLEEPLM |
| SEQ ID NO: 103 | HLGLEEPLY |
| SEQ ID NO: 104 | HLGLEEPLN |
| SEQ ID NO: 105 | HLGLEEPLQ |
| SEQ ID NO: 106 | HLGLEEPFV |
| SEQ ID NO: 107 | HLGLEEPFQ |
| SEQ ID NO: 108 | HLGLEEPFN |
| SEQ ID NO: 109 | HLGLEEPVM |
| SEQ ID NO: 110 | HLGLEEPVN |
| SEQ ID NO: 111 | HLGLEEPMK |

In some instances, the analogs of HBD1 or fragments thereof may differ in sequence from HBD1 by 1, 2, 3, 4, 5, 6, 7, 8 or 9 amino acid substitutions, deletions, or additions, or combinations thereof. In some instances, the amino acid substitution is a conservative amino acid substitution. As used herein the expression "conservative amino acid substitution" refers to substitutions that substitute a residue with another of like characteristics. Typical conservative amino acid substitutions include those among Gly (G), Ala (A), Val (V), Leu (L) and Ile (I); those among Ser (S), Cys (C), Met (M) and Thr (T); those among the acidic residues Asp (D) and Glu (E); those among Asn (N) and Gln (Q); those among the basic residues His (H), Lys (K) and Arg (R); and those among the aromatic residues Phe (F), Try (W) and Tyr (Y). In some embodiments, the present technology provides an isolated peptide having a fragment of HBD1 as set forth in SEQ ID NO: 1. In some instances, the fragment is between 6 to 10 amino acids in length and comprises residues 3 to 10 of HBD1, namely: HLGLEEPK as set forth in SEQ ID NO: 7 or an analog thereof. Examples of analogs of a peptide having the amino acid sequence HLGLEEPK include, but are not limited to the peptides presented in Table 4.

TABLE 4

Analogs of HBD1 (3-10) fragment with amino acid substitutions at various positions

| SEQ ID NO: | Amino Acid Sequence |
| --- | --- |
| SEQ ID NO: 112 | HLGLEEP<u>R</u> |
| SEQ ID NO: 113 | HLGLEEP<u>H</u> |

In some embodiments, the present technology provides an isolated peptide having a fragment of HBD1 as set forth in SEQ ID NO: 1. In some instances, the fragment is between 6 to 10 amino acids in length and comprises residues 5 to 10 of HBD1, namely: GLEEPK as set forth in SEQ ID NO: 14 or an analog thereof. In some other embodiments, the fragment is between 6 to 9 amino acids in length and comprises residues 5 to 10 of HBD1, namely: GLEEPK as set forth in SEQ ID NO: 14 or an analog thereof. Examples of analogs of a peptide having the amino acid sequence GLEEPK include, but are not limited to the peptides presented in Table 5.

TABLE 5

Analogs of HBD1 (5-10) fragment with amino acid substitutions at various positions

| SEQ ID NO: | Amino Acid Sequence |
| --- | --- |
| SEQ ID NO: 79 | GLEEP<u>L</u> |
| SEQ ID NO: 80 | GLEEP<u>R</u> |
| SEQ ID NO: 81 | GL<u>D</u>EPK |
| SEQ ID NO: 82 | GLE<u>D</u>PK |
| SEQ ID NO: 83 | G<u>G</u>EEPK |
| SEQ ID NO: 84 | G<u>V</u>EEPK |
| SEQ ID NO: 85 | G<u>I</u>EEPK |
| SEQ ID NO: 86 | <u>V</u>LEEPK |
| SEQ ID NO: 87 | <u>L</u>LEEPK |
| SEQ ID NO: 88 | <u>I</u>LEEPK |

In some other embodiments, the peptides of the present disclosure may be modified. As used herein the term "modified" when used to qualify a peptide, refers to any changes made to a peptide, such as changes to the length of the peptide, the amino acid sequence, chemical structure, co-translational modification, or post-translational modification of a peptide. In some instances, the peptides of the present disclosure comprise one or more amino acid residues that are modified.

As used herein, the expression "post-translational modification" refers to any modification of a natural or non-natural amino acid that occurs to such an amino acid after it has been incorporated into a peptide chain. The term encompasses, by way of example only, co-translational in vivo modifications, co-translational in vitro modifications (such as in cell-free translation system), post-translational in vivo modifications, and post-translational in vitro modifications. Examples of post-translational modifications are, but are not limited to, glycosylation, pegylation, acetylation, acylation, amidation, methylation, carboxylation, phosphorylation, addition of salts, amides or esters, in particular C-terminal esters, and N-acyl derivatives of the peptides of the present disclosure. These types of post-translational modifications are well known in the art.

In some embodiments, the peptides of the present disclosure include one or more poly(ethylene glycol) (or "PEG") moiety of between about 10,000 and about 40,000 molecular weight coupled to either the N- or C-terminus of the peptide. "Polyalkylene glycol" means straight or branched polyalkylene glycol polymers including, but not limited to, polyethylene glycol (PEG), polypropylene glycol (PPG), and polybutylene glycol (PBG), as well as co-polymers of PEG, PPG and PBG in any combination, and includes the mono-alkylether of the polyalkylene glycol. Thus, in various embodiments of the present technology, the polyalkylene glycol in the peptides of the present disclosure can be, but is not limited to, polyethylene glycol, polypropylene glycol, polybutylene glycol, and any combination thereof. In certain embodiments, the polyalkylene glycol is polyethylene glycol or "PEG." The term "PEG subunit" refers to a single polyethylene glycol unit, i.e., —($CH_2CH_2O$)—.

In some embodiments, the polyalkylene glycol (e.g., PEG) can be non-polydispersed, monodispersed, substantially monodispersed, purely monodispersed, or substantially purely monodispersed. "Monodispersed" is used to describe a mixture of compounds wherein about 100 percent of the compounds in the mixture have the same molecular weight. "Substantially monodispersed" is used to describe a mixture of compounds wherein at least about 95 percent of the compounds in the mixture have the same molecular weight. "Purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture. "Substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture. Table 6 presents examples of peptides of the present disclosure that are modified by pegylation.

TABLE 6

PEGylated HBD1 fragments

| SEQ ID NOs | Amino Acid Sequence |
|---|---|
| SEQ ID NO: 63 | PEG20-C-KHHLGLEEPKKLR |
| SEQ ID NO: 64 | KHHLGLEEPKKLR-C-PEG20 |
| SEQ ID NO: 65 | PEG20-C-HHLGLEEPKK |
| SEQ ID NO: 66 | HHLGLEEPKK-C-PEG20 |
| SEQ ID NO: 67 | PEG20-C-HLGLEEPKK |

In some other instances, the peptides of the present disclosure include one or more acyl group(s) coupled to any amino acid of the peptide. In some instances, the one or more acyl group(s) is coupled to the N-terminal or the C-terminal amino acid or to both. In some instances, acylation of the peptides of the present disclosure is a fatty acylation by which a fatty acid is added to one or more particular amino acid(s) of the peptide. Examples of fatty acylation include addition of: lauric acid (C12:0), tridecylic acid (C13:0), myristic acid (C14:0), pentadecylic acid (C15:0), palmitic acid (C16:0), margaric acid (C17:0), stearic acid (C18:0), nonadecyclic acid (C19:0), arachidinic acid (C20:0), heneicosylic acid (C21:0), behenic acid (C22:0), tricosylic acid (C23:0), or lignoceric acid (C24:0), or a mixture thereof to one or more amino acid of the peptides of the present disclosure.

In some variants, the fatty acid to be added may be unsaturated (e.g., monounsaturated or polyunsaturated). Examples of unsaturated fatty acids include but are not limited to: i) mono-unsaturated fatty acid:crotonic acid, myristoleic, palmitoleic acid, sapienic acid, oleic acid, elaidic acid, vaccenic acid, gadoleic, eicosenoic acid, erucic acid, nervonic acid; ii) di-unsaturated fatty acid: linoleic acid, eicosadienoic acid, docosadienoic acid; iii) tri-unsaturated fatty acids: linolenic acid, pinolenic acid, eleostearic acid, mead acid, dihomo-γ-linolenic acid, eicosatrienoic acid; iv) tetra-unsaturated fatty acid: stearidonic acid, arachidonic acid, eicosatetraenoic acid, adrenic acid; v) pentaunsaturated fatty acids: bosseopentaenoic acid, eicosapentaenoic acid, ozubondo acid, sardine acid, tetracosanolpentaenoic acid; and vi) hexa-unsaturated fatty acids: docosahexaenoic acid, and herring acid. In some embodiments, the peptides of the present disclosure may be coupled to fatty acids that comprise one or more carboxylic functional groups (—COOH). The methods for carrying acylation of peptides are well known in the art. Table 7 presents examples of peptides of the present disclosure that are modified by acylation.

TABLE 7

Acylated HBD1 (2-11) fragments

| SEQ ID NOs | Amino Acid Sequence |
|---|---|
| SEQ ID NO: 68 | C16:0-HHLGLEEPKK |
| SEQ ID NO: 69 | C18:0-HHLGLEEPKK |
| SEQ ID NO: 70 | C20:0-HHLGLEEPKK |
| SEQ ID NO: 71 | C14:0-HLGLEEPKK |
| SEQ ID NO: 72 | C16:0-HLGLEEPKK |

TABLE 7-continued

Acylated HBD1 (2-11) fragments

| SEQ ID NOs | Amino Acid Sequence |
|---|---|
| SEQ ID NO: 73 | C18:0-HLGLEEPKK |
| SEQ ID NO: 74 | C20:0-HLGLEEPKK |
| SEQ ID NO: 75 | C16:0-diacid-HLGLEEPKK |
| SEQ ID NO: 76 | HLGLEEPKK-C16:0 |
| SEQ ID NO: 78 | C16:0-KHHLGLEEPKKLR |

In some additional embodiments, the peptides of the present disclosure may be coupled to a linker or a linker group (e.g., linker moiety). As used herein, the expression "linker" or "linking group" includes non-amino acid linking groups such as are known in the art (see, e.g., U.S. Pat. Nos. 7,468,418; 7,402,652; and 7,351,797, which are all incorporated herein by reference) or variations thereof that will be apparent to those skilled in the art.

In some embodiments, the peptides of the present disclosure may include more than one modification (e.g., may include a PEG group and an acyl group).

In some other embodiments, the peptides of the present disclosure may be coupled to a modifying group which is itself modified. For example, the peptides of the present disclosure may be coupled to a fatty acid which is itself modified. The modified fatty acid may, for example, be coupled to a linker or a linker group and the linker or the linker group may itself be coupled to another modifying group such as a PEG group or one or more carboxylic functional groups (—COOH). Various combinations of modifications and the methods for achieving them will be recognized and appreciated by those skilled in the art.

Certain aspects of the present technology use polynucleotides. These polynucleotides include isolated polynucleotides which encode the HBD1 peptides, fragments and analogs defined herein.

As used herein, the term "polynucleotide" refers to a molecule comprised of a plurality of deoxyribonucleotides or nucleoside subunits. The linkage between the nucleoside subunits can be provided by phosphates, phosphonates, phosphoramidates, phosphorothioates, or the like, or by nonphosphate groups as are known in the art, such as peptoid-type linkages utilized in peptide nucleic acids (PNAs). The linking groups can be chiral or achiral. The oligonucleotides or polynucleotides can range in length from 2 nucleoside subunits to hundreds or thousands of nucleoside subunits. While oligonucleotides are preferably 5 to 100 subunits in length, and more preferably, 5 to 60 subunits in length, the length of polynucleotides can be much greater (e.g., up to 100). The polynucleotide may be any of DNA and RNA. The DNA may be in any form of genomic DNA, a genomic DNA library, cDNA derived from a cell or tissue, and synthetic DNA. Moreover, the present disclosure may, in certain aspects, use vectors which include bacteriophage, plasmid, cosmid, or phagemid.

The polypeptides useful in the present technology may be prepared in any suitable manner as known in the art. Such polypeptides include isolated naturally occurring polypeptides, recombinantly produced polypeptides, synthetically produced polypeptides, or polypeptides produced by a combination of these methods. Means and methods for preparing such polypeptides are well known in the art.

B. Therapeutic Actions

As used herein, the terms "treat," "treating" and "treatment" as used herein all refer to any type of treatment that imparts a benefit to a subject afflicted with a disease, including improvement in the condition of the patient (e.g., in one or more symptoms), delay in the progression of the disease, or the like.

As used herein, the term "modulation" or the term "modulating" refers to both upregulation (i.e., activation or stimulation) and downregulation (i.e., inhibition or suppression) of a response, or the two in combination or apart.

As used herein, the terms "subjects" or "patient" generally relates a mammalian or non-mammalian animal including, for example and without limitation, a human, a rat, a mouse or farm animal. Reference to a subject does not necessarily indicate the presence of a disease or disorder. The term "subject" includes, for example, a mammalian or non-mammalian animal being dosed with a peptide of the present technology as part of an experiment, a mammalian or non-mammalian animal being treated to help alleviate a disease or disorder, and a mammalian or non-mammalian animal being treated prophylactically to retard or prevent the onset of a disease or disorder. Subject mammals may be human subjects of any age, such as an infant, a child, an adult or an elderly adult.

In some embodiments, the peptides of the present disclosure may be used for controlling, regulating, modulating, preventing, improving, ameliorating, and/or treating metabolic disorders. As used herein, the expression "metabolic disorders" refers to, but is not limited to, disorders associated with abnormal or impaired metabolic processes. Examples of metabolic disorders include, but are not limited to, disorders associated with impaired acid-base imbalance, disorders associated with impaired calcium metabolism, disorders associated with impaired glucose metabolism, disorders associated with impaired carbohydrate metabolism, disorders associated with impaired iron metabolism, disorders associated with impaired lipid metabolism, malabsorption syndromes, metabolic syndrome, disorders associated with impaired leptin metabolism, disorders associated with impaired insulin metabolism, and disorders associated with impaired insulin-like growth factor metabolism.

In some embodiments, the peptides of the present disclosure may be used for modulating glucose metabolism. In some implementations of these embodiments, the peptides of the present technology may be used for modulating glucose metabolism in subjects that are afflicted with a disorder associated with impaired glucose metabolism. In some other implementations of these embodiments, the peptides of the present technology may be used for controlling, regulating, modulating, preventing, improving, ameliorating, and/or treating a disorder associated with impaired glucose metabolism in a subject.

As used herein, the expression "disorder associated with impaired glucose metabolism" refers to a disorder in which plasma glucose is not maintained within the normal range. Examples of disorders associated with impaired glucose metabolism include, but are not limited to: hypoglycemia; hyperglycemia; carbohydrate intolerance; glucose intolerance; impaired fasting glucose; impaired glucose tolerance; carbohydrate-lipid metabolism disturbance; hyperinsulinemia; Type IV hyperlipoproteinemia; insulin resistance; diabetes Type I; diabetes Type II; obesity; impaired beta cell function and acromegaly; rare genetic disorders of obesity such as, but not limited to: disorders associated with impaired melanocortin-4 (MC4) signaling pathway, leptin receptor (LEPR) deficiency, LEPR mutations, leptin receptor-related monogenic obesity, syndrome of extreme insulin resistance; proopiomelanocortin (POMC) deficiency, POMC heterozygous, Alström syndrome, Bardet-Biedl syndrome (BBS), Donohue syndrome (leprechaunism), Rabson-Mendenhall syndrome, syndrome of extreme insulin resistance type A, type B, type C, HAIR-AN, Polycystic Ovary syndrome (PCOS), congenital lipodystrophy syndromes, Beradinelli-Seip syndrome, acquired lipodystrophy syndromes, generalized lipodystrophy, and partial lipodystrophy.

Is some instances, the metabolic disorder is a disorder associated with impaired insulin metabolism. As used herein, the expression "disorder associated with impaired insulin metabolism" refers to a disorder associated with one of: synthesis, circulation and degradation of insulin, as well as to disorders associated with impaired pancreatic functions. Examples of disorders associated with impaired insulin metabolism include, but are not limited to, metabolic syndrome, dyslipidemia, atherosclerosis, hypertension, obesity, hyperinsulinemia, glucose intolerance, hypertension, peripheral arterial disease, type A syndrome, type B syndrome, endothelial dysfunction, diabetes, microalbuminuria, and impaired fibrinolysis.

As used herein, the expression "metabolic syndrome" refers to a multiplex risk factor that arises from insulin resistance accompanying abnormal adipose deposition and function. It is comprised of a combination of risk factors for coronary heart disease, as well as for diabetes, fatty liver, and several cancers. Clinical manifestations of metabolic syndrome include the following: hypertension, hyperglycemia, hypertriglyceridemia, reduced high-density lipoprotein cholesterol (HDL-C), abdominal obesity, chest pain or shortness of breath: Suggesting the rise of cardiovascular and other complications, acanthosis nigricans, hirsutism, peripheral neuropathy, retinopathy, xanthomas and xanthelasmas.

In some embodiments, the peptides of the present disclosure may be used to lower plasma glucose levels in a subject, and/or to improve overall tolerance and/or resistance of a subject to glucose. In some implementations of these embodiments, the peptides of the present disclosure may be used in the management of diabetes in a subject. In some implementations of these embodiments, the peptides of the present disclosure may be used in the prevention of diabetes in a subject. In some implementations of these embodiments, the peptides of the present disclosure may be used in the treatment of diabetes in a subject. In some implementations of these embodiments, the diabetes is Type I diabetes. In some other implementations of these embodiments, the diabetes is Type II diabetes.

In some embodiments, the peptides of the present disclosure may be used for regulating insulin metabolism. For example, the peptides of the present disclosure may be used to increase insulin secretion, increase insulin sensitivity, decrease insulin resistance, and/or overcome insulin deficiency.

In some embodiments, the peptides of the present technology may be used for controlling, regulating, modulating, preventing, improving, ameliorating, and/or treating hypoglycemia; hyperglycemia; carbohydrate intolerance; glucose intolerance; impaired fasting glucose; impaired glucose tolerance; carbohydrate-lipid metabolism disturbance; hyperinsulinemia; Type IV hyperlipoproteinemia; insulin resistance; diabetes Type I; diabetes Type II; obesity; impaired beta cell function and acromegaly; rare genetic disorders of obesity such as, but not limited to: disorders associated with impaired melanocortin-4 (MC4) signaling pathway, leptin receptor (LEPR) deficiency, LEPR mutations, leptin receptor-related monogenic obesity, syndrome of extreme insulin resistance; proopiomelanocortin (POMC) deficiency, POMC heterozygous, Alström syndrome, Bardet-Biedl syndrome (BBS), Donohue syndrome (leprechaunism), Rabson-Mendenhall syndrome, syndrome of extreme insulin resistance type A, type B, type C, Polycystic Ovary syndrome (PCOS), congenital lipodystrophy syndromes, Beradinelli-Seip syndrome, acquired lipodystrophy syndromes, generalized lipodystrophy, and partial lipodystrophy.

In some embodiments, the uses and methods defined herein comprise administering to a subject a therapeutically effective amount of a peptide as defined herein to achieve the effects discussed here. As used herein, the expression "therapeutically effective amount" refers to the amount of peptides of the present disclosure which is effective for producing some desired therapeutic effect as defined herein at a reasonable benefit/risk ratio applicable to any medical treatment.

Therapeutically effective dosage of any specific peptide of the present disclosure will vary from peptide to peptide, subject to subject, and patient to patient, and will depend, among other things, upon the effect or result to be achieved, the condition of the patient and the route of delivery. In some embodiments, a dosage is from about 0.01 µg/kg to about 100 mg/kg, from about 0.01 µg/kg to about 50 mg/kg, from about 0.01 µg/kg to about 10 mg/kg, from about 0.01 µg/kg to about 5 mg/kg, from about 0.1 µg/kg to about 100 mg/kg, from about 0.1 µg/kg to about 50 mg/kg, from about 0.1 µg/kg to about 10 mg/kg, from about 0.1 µg/kg to about 5 mg/kg, from about 1 µg/kg to about 100 mg/kg, from about 1 µg/kg to about 50 mg/kg, from about 1 µg/kg to about 10 mg/kg, from about 1 µg/kg to about 5 mg/kg, from about 10 µg/kg to about 100 mg/kg, from about 10 µg/kg to about 50 mg/kg, from about 10 µg/kg to about 10 mg/kg, from about 10 µg/kg to about 5 mg/kg, from about 100 µg/kg to about 100 mg/kg, from about 100 µg/kg to about 50 mg/kg, from about 100 µg/kg to about 10 mg/kg, from about 100 µg/kg to about 5 mg/kg, In some instances, the dosage is from about 0.001 mg/kg, about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg or about 1.0 mg/kg, up to about 30 mg/kg, or about 40 mg/kg. In some other instances, the dosage is about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, about 49 mg/kg, or about 50 mg/kg or more may be used. Additional examples of therapeutically effective dosages include: between about 1 and about 50 mg/kg/96 hr; between about 1 and about 50 mg/kg/48 hr; between about 1 and about 50 mg/kg/36 hr; between about 1 and about 50 mg/kg/24 hr; between about 1 and about 50 mg/kg/12 hr; between about 1 and about 25 mg/kg/96 hr; between about 1 and about 25 mg/kg/48 hr; between about 1 and about 25 mg/kg/36 hr; between about 1 and about 25 mg/kg/24 hr; between about 1 and about 25 mg/kg/12 hr; between about 1 and about 10 mg/kg/96 hr; between about 1 and about 10 mg/kg/48 hr; between about 1 and about 10 mg/kg/36 hr; between about 1 and about 10 mg/kg/24 hr; between about 1 and about 10 mg/kg/12 hr; between about 1 and about 5 mg/kg/96 hr; between about 1 and about 5 mg/kg/48 hr; between about 1 and about 5 mg/kg/36 hr; between about 1 and about 5 mg/kg/24 hr; between about 1 and about 5 mg/kg/12 hr; between about 0.001 and about 1 mg/kg/96 hr; between about 0.001 and about 1 mg/kg/48 hr; between about 0.001 and about 1 mg/kg/36 hr; between about 0.001 and about 1 mg/kg/24 hr; and between about 0.001 and about 1 mg/kg/12 hr.

"Concurrently administering" or "concurrently administer" as used herein means that the two or more peptides, compounds or compositions are administered closely enough in time to produce a combined effect (that is, concurrently may be simultaneously, or it may be two or more events occurring within a short time period before or after each other, e.g., sequentially). Simultaneous concurrent administration may be carried out by, for example, mixing the compounds prior to administration, or by administering the compounds at the same point in time but at different anatomic sites and/or by using different routes of administration.

C. Pharmaceutical Compositions

As used herein, the expression "active agent" refers to a peptide as defined herein.

The expressions "therapeutically acceptable", "therapeutically suitable", "pharmaceutically acceptable" and "pharmaceutically suitable" are used interchangeably herein and refer to a peptide, a compound, or a composition that is suitable for administration to a subject to achieve the effects described herein, such as the treatment defined herein, without unduly deleterious side effects in light of the severity of the disease and necessity of the treatment.

The peptides described above may be formulated for administration in a pharmaceutical carrier in accordance with known techniques. See, e.g., Remington, The Science And Practice of Pharmacy (9th Ed. 1995). In the manufacture of a pharmaceutical composition according to the present disclosure, the peptide (including the physiologically acceptable salts thereof) is typically admixed with, inter alia, an acceptable carrier. The carrier must, of course, be acceptable in the sense of being compatible with any other ingredients in the composition and must not be deleterious to the patient. The carrier may be a solid or a liquid, or both, and is preferably formulated with the peptide as a unit-dose formulation, for example, a tablet, which may contain from about 0.01 or about 0.5% to about 95% or about 99% by weight of the peptide. One or more active compounds may be incorporated in the compositions of the present disclosure, which may be prepared by any of the well-known techniques of pharmacy comprising admixing the components, optionally including one or more accessory ingredients.

The composition of the present disclosure include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular peptide which is being used.

Compositions suitable for oral administration may be presented in discrete units, such as capsules, cachets, lozenges, or tablets, each containing a predetermined amount of the peptide; as a powder or granules; as a solution or a suspension in an aqueous or non-aqueous liquid; or as an oil-in-water or water-in-oil emulsion. Such compositions may be prepared by any suitable method of pharmacy which includes the step of bringing into association the peptide and a suitable carrier (which may contain one or more accessory ingredients as noted above). In general, the compositions of the present disclosure are prepared by uniformly and intimately admixing the peptide with a liquid or finely divided solid carrier, or both, and then, if necessary, shaping the resulting mixture. For example, a tablet may be prepared by compressing or molding a powder or granules containing the peptide, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Compositions suitable for buccal (sub-lingual) administration include lozenges comprising the peptide in a flavoured base, usually sucrose and acacia or tragacanth; and pastilles comprising the peptide in an inert base such as gelatin and glycerin or sucrose and acacia.

Compositions of the present disclosure suitable for parenteral administration comprise sterile aqueous and non-aqueous injection solutions of the peptide, which preparations are preferably isotonic with the blood of the intended recipient. These preparations may contain anti-oxidants, buffers, bacteriostats and solutes which render the composition isotonic with the blood of the intended recipient. Aqueous and non-aqueous sterile suspensions may include suspending agents and thickening agents. The composition may be presented in unit \dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present disclosure, there is provided an injectable, stable, sterile composition comprising a peptide as defined herein, or a salt thereof, in a unit dosage form in a sealed container. The peptide or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the peptide or salt. When the peptide or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Compositions suitable for rectal administration are preferably presented as unit dose suppositories. These may be prepared by admixing the peptide as defined herein with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, for example, Pharmaceutical Research 3 (6):318 (1986)) and typically take the form of an optionally buffered aqueous solution of the peptide as defined herein. Suitable compositions comprise citrate or bis\tris buffer (pH 6) or ethanol/water and contain from 0.1M to 0.2M active ingredient.

Further, the present disclosure provides liposomal formulations of the peptide disclosed herein and salts thereof. The technology for forming liposomal suspensions is well known in the art. When the peptide as defined herein or salt thereof is an aqueous-soluble salt, using conventional liposome technology, the same may be incorporated into lipid vesicles. In such an instance, due to the water solubility of the peptide or salt, the peptide or salt will be substantially entrained within the hydrophilic center or core of the liposomes. The lipid layer employed may be of any conventional composition and may either contain cholesterol or may be cholesterol-free. When the peptide or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

The liposomal formulations containing the active agents disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble active agent disclosed herein, or salts thereof, such as aqueous base emulsions. In such an instance, the composition will contain a sufficient amount of pharmaceutically acceptable emulsifying agent to emulsify the desired amount of the active agent or salt thereof. Particularly useful emulsifying agents include phosphatidyl cholines, and lecithin.

In some embodiments, the peptides of the present disclosure may be delivered to a subject in need thereof using a medical device, in particular using orthopedic medical devices. Examples of medical devices that may be useful for delivering the peptides of the present disclosure include, but are not limited to, sponges (e.g., collagen sponges, gelatin sponges, or the like), dressing, gauges, stents, cages (e.g., intervertebral cages, fusion cages, or the like), bone cement, bone mixers, bone substitutes, pins, anchors, buttons, prostheses, screws (e.g., facet screws, pedicle screw systems, bone screws, or the like), spacers, intramedullary nails, stems (e.g., hip stems or the like), custom implants, plates (e.g., humerous plates, wrist plates, radius plates, cervical plates, lumbar plates or the like), and trauma products. In these embodiments, the peptides of the present disclosure may be incorporated into the materials used to make the medical device or may be applied onto the materials used to make the medical devices or onto the medical device itself.

In some other embodiments, the peptides of the present disclosure may be delivered to a subject in need thereof using a delivery device such as a particle (e.g., nanoparticles or microparticles) or an encapsulation system (e.g., microcapsules, microspheres). In some instances, the peptides of the present disclosure may be dispersed throughout the materials forming the delivery systems, such as for example, polymeric chains, or may be located into pores or cavities formed into the delivery system. In some instances, the release of the peptides from such delivery systems may be controlled (i.e., slow release, sustained release or controlled release). Examples of particles and particles and encapsulation systems that may be used to deliver the peptides of the present disclosure are well known in the art.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use.

In some embodiments, the present technology provides for kits comprising one or more peptides as defined herein together with instructions for use of kit according to the applications defined herein.

Identification of equivalent peptides, compounds, compositions, methods, uses and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of various embodiments of the present technology. They are not intended to limit or define the entire scope of this technology. It should be appreciated that the technology is not limited to the particular embodiments described and illustrated herein but includes all modifications and variations falling within the scope of the disclosure as defined in the appended embodiments.

Example 1: HBD1 Peptide Improves Glucose Tolerance In Vivo

After being acclimatized 7 days to the laboratory conditions, nine-week-old male B6. V-Lepob/J. mice (Charles River) were subcutaneously administered with vehicle (NaCl 0.9%) or with a peptide as set forth in SEQ ID NO: 73 (C18:0-HLGLEEPKK) at 3 mg/kg (n=5 animals for each group) twice daily for 15 days. On day 15, fasted (overnight) mice were injected intraperitoneally with glucose at 1 g/kg. Plasma blood glucose (expressed as mmol/L) was recorded at 45 minutes post glucose injection. The results are presented in FIG. 1. The results show that administration of the HBD1 peptide reduced the plasma glucose levels in response to the IP glucose tolerance test, thereby suggesting a role for HBD1 peptides in glycemic control. These results support the use of HBD1 peptides for the treatment of clinical conditions associated with glucose intolerance or insulin resistance, such as, but not limited to, type 2 diabetes, leptin deficiency, leptin receptor deficiency, and extreme insulin resistance syndromes.

Example 2: Effects of HBD1 Peptides on Glucose Tolerance in Leptin Deficient Mice To further assess the effects of HBD1 peptides on glucose and insulin metabolisms, basal blood glucose and glucose response to an intraperitoneal glucose tolerance test (IP-GTT) were assessed in glucose-telemetered obese ob/ob mice after twice daily administration of HBD peptides for 28 consecutive days. Implantation of glucose telemetry device (HD-XG, Data Science International) was carried out according to known protocols.

A dose of HBD peptide fragment of SEQ ID NO: 73 (C18:0-HLGLEEPKK) was administered twice daily at 8-hour±1 hour interval between the two daily administrations. 24 V-Lepob/J (Ob/Ob) male mice (The Jackson Laboratory, Farmington, Conn. USA) were administered subcutaneously with vehicle (NaCl 0.9%) (Control group) or with the peptide at 1 and 3 mg/kg (Test groups) (n=5-8 animals for each group) twice daily for 28 days. The first day of dosing was designated as Day 1. Bolus injection was carried out using a sterile syringe and the needle was introduced subcutaneously, 2 to 4 injection sites were used in rotation. The hair of the animals on the injection area was clipped prior to the first injection and then as necessary during the treatment period. The volume administered was 5 mL/kg/administration. Individual dose volumes were calculated using the latest body weight. On day 27, 16-hour mean blood glucose levels were assessed in normal fed conditions. On day 28, fasted (4 hours) mice were injected intraperitoneally with glucose at 1 g/kg. Plasma blood glucose profile (expressed as mg/dL) was recorded every minute up to 3-hour post glucose injection.

Intraperitoneal glucose tolerance test (IPGTT)—On the morning of the IGPTT day (day 28), 2-hour fasted animals were treated with vehicle or with the HBD fragment. Glucose solution was administered 2 hours±15 minutes post-dosing (vehicle or a peptide as set forth in SEQ ID NO: 73 (C18:0-HLGLEEPKK). Blood glucose was monitored from 10 minutes before (fasting condition) to 3-hour post-glucose challenge. Food was re-introduced 4 hours post-glucose challenge. The second treatment of the day (the HBD fragment or vehicle) was performed 2 hours after food re-introduction.

Figure 2A:
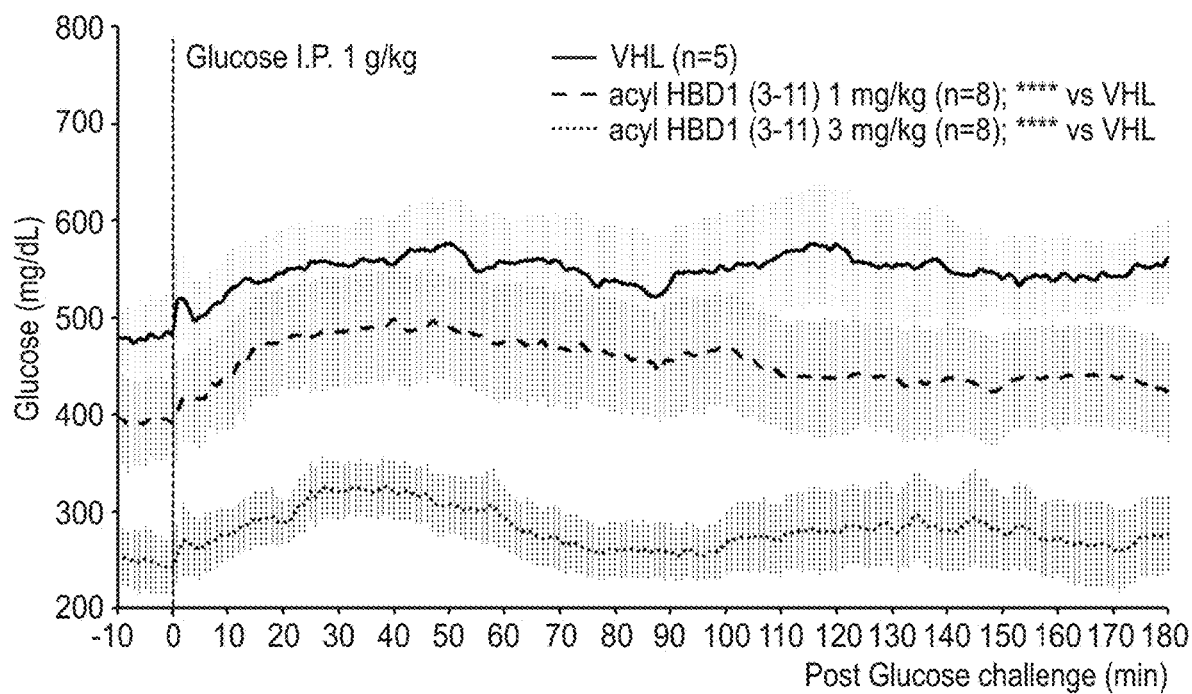
FIGS. 2A-2C show graphs indicating that a HBD1 fragment according to one embodiment of the present technology improves glucose intolerance in glucose telemetered ob/ob mice, a mouse model with leptin deficiency leading to insulin resistance.
Figure 2B:
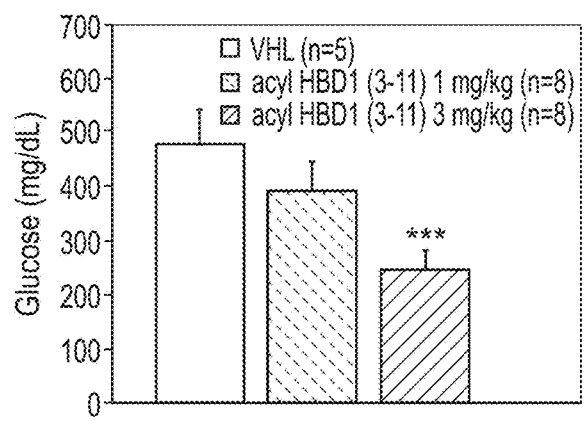
Figure 2C:
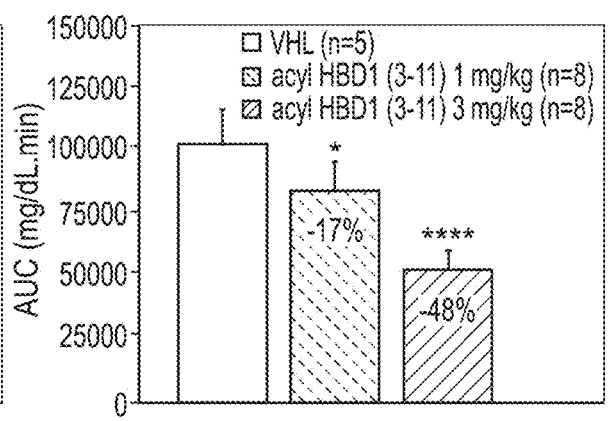
Figure 3A:
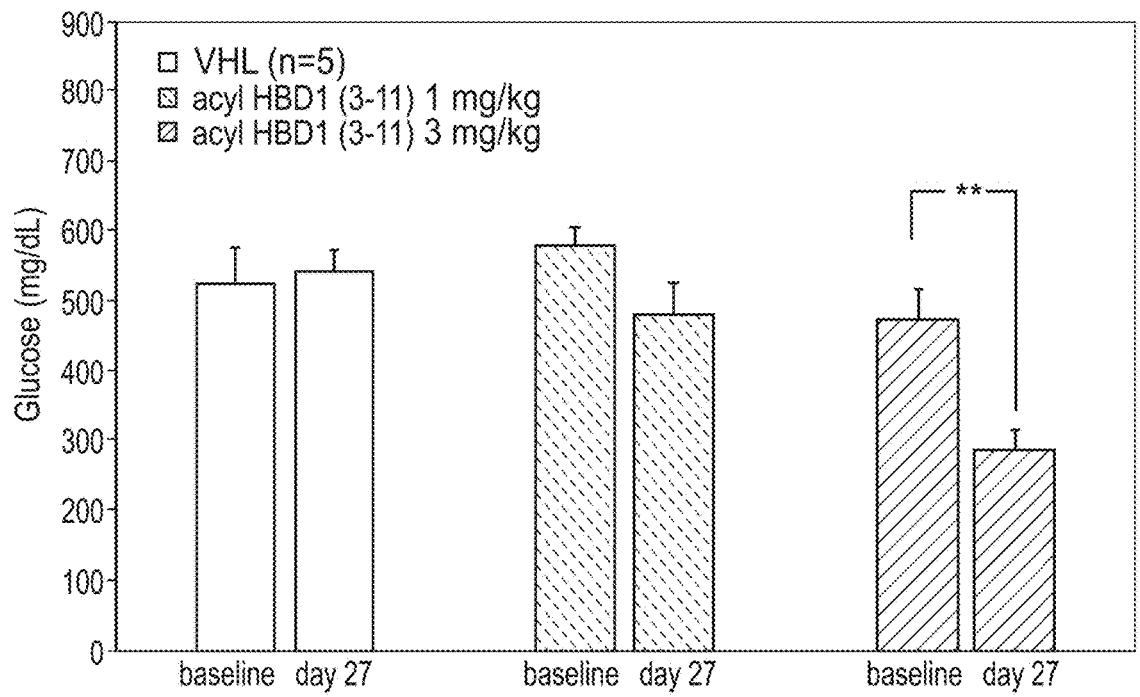
FIGS. 3A-3B show graphs indicating that a HBD1 fragment according to one embodiment of the present technology improves glucose intolerance in glucose telemetered ob/ob mice, a mouse model with leptin deficiency leading to insulin resistance.
Figure 3B:
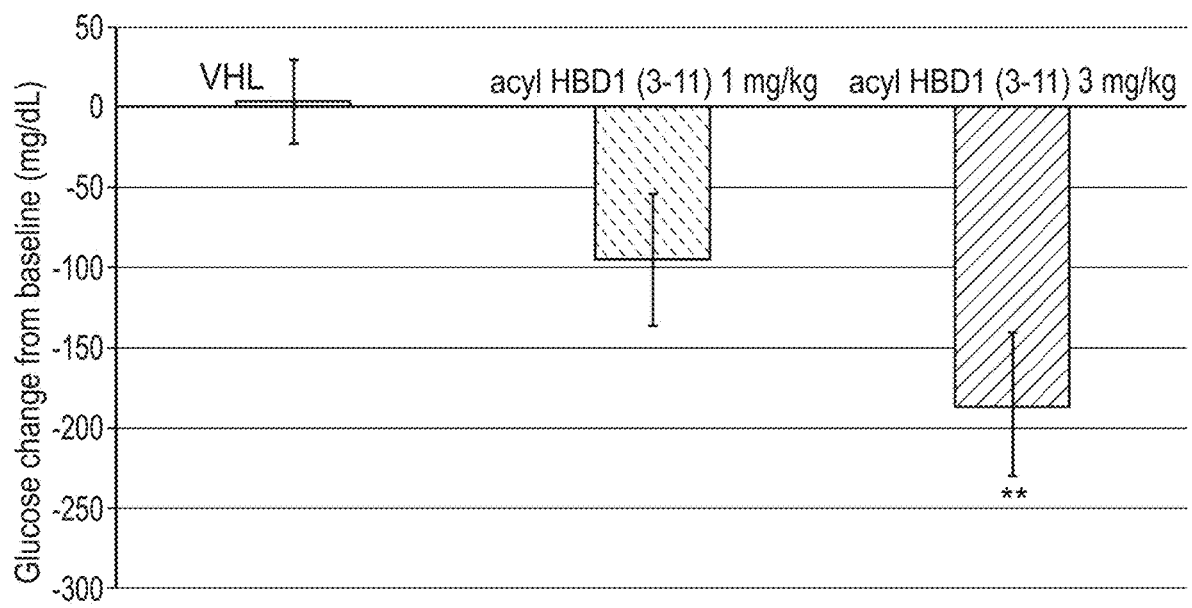

The results, which are presented in FIG. 2 and FIGS. 3A-3B, indicate that HBD1 fragment SEQ ID NO: 73 improved glucose intolerance in a dose-dependent manner in glucose telemetered ob/ob mice, a mouse model with leptin deficiency leading to insulin resistance and glucose intolerance. FIG. 2 shows that, after 4 weeks of administration, the test peptide decreased fasting glucose levels and glucose excursion following IPGTT. A marked effect was observed at the dose of 3 mg/kg. FIGS. 3A-3B also show a positive effect on glucose control, as the test peptide was able to markedly decrease 16-hour average blood glucose levels in these mice exhibiting severe hyperglycemia at baseline.

Example 3: Effects of HBD1 Peptides on Glucose Uptake by Adipose Cells In Vitro

To further test the effects of HBD1 peptides on glucose metabolism, the ability of HBD1 peptides to increase glucose uptake by cultured, fully-differentiated 3T3-LI adipocytes was examined. 3T3-LI cells are a mouse fibroblast cell line which when cultured under specific conditions, differentiate into adipocytes.

Differentiation of 3T3-LI cells into adipocytes was achieved using the following protocol. 3T3-L1 cells were seeded in 24-well plates and cultured in 3T3-L1 maintenance medium (DMEM containing 10% fetal bovine serum, 4 mM L-glutamine 1 mM, sodium pyruvate) until the cells were 100% confluent. The cells were then fed with 3T3-L1 maintenance medium and cultured for a further 48 h. To initiate differentiation into adipocytes, the medium was changed to Differentiation medium 1 (DMEM containing 10% fetal bovine serum, 4 mM L-glutamine, 1 mM sodium pyruvate, 0.5 mM IBMX, 0.25 mM dexamethasone 1 mg/ml insulin), and cultured for a further 2 days. The medium was then changed to Differentiation medium 2 (DMEM containing 10% fetal bovine serum, 4 mM L-glutamine, 1 mM sodium pyruvate, 1 mg/ml insulin), and cultured for a further 2 days. The medium was then changed to Adipocyte Maintenance medium (DMEM containing 10% fetal bovine serum, 4 mM L-glutamine, 1 mM sodium pyruvate), and cultured for a further 7 days. During this time, the medium was changed every other day. The now fully differentiated adipocytes were utilized for glucose uptake experiments (day 11 from initiation of differentiation). Stock solutions of the HBD1 peptides to be tested were prepared by dilution with 0.9% NaCl solution under sterile conditions in a laminar flow cabinet to a concentration of 1 mg/ml, based on net peptide content. The solutions were homogenized by gentle inversion. Test items were prepared from the stock solutions, and remaining stock solution was aliquoted and stored at −20° C. and used without repeated freeze-thaw cycles.

Glucose uptake experiments were carried our using the following protocol. Prior to beginning the experiment, 100 ml of Krebs Ringer bicarbonate buffer (KRBB)(25 mM Hepes pH 7.4, 118 mM NaCl, 5 mM NaHCO$_3$, 4.7 mM KCl, 1.2 mM KH$_2$PO$_4$, 1.2 mM MgSO$_4$, 2.5 mM CaCl$_2$, 0.2% BSA—Filtered using a 0.2 µm filter) and 100 ml of Incubation medium (DMEM containing 4 mM L-glutamine, 1 mM sodium pyruvate, 1% penicillin streptomycin, 0.2% BSA—Filtered using a 0.2 µm filter) were pre-warmed to 37° C., and 500 ml of KRBB was chilled on ice. Stock solutions of test compounds were diluted to 3 µg/ml final concentrations in pre-warmed Incubation medium and in pre-warmed KRBB. Insulin (positive control), previously diluted 1:1000 in sterile 0.9% NaCl, was further diluted in 10 ml of both medium and buffer to a final concentration of 1 nM. All traces of the medium were carefully removed from the cells using a fine tip. 1 ml of incubation medium containing study compounds or vehicle was added to the appropriate wells. No insulin was added at this time. The plate was incubated at 37° for 24 h. After the incubation period was complete, media was removed from wells, and the cells in appropriate wells were washed with 300 µl pre-warmed KRBB containing either appropriate test substance or vehicle. The wash buffer was then removed from the cells and replaced with 270 µl pre-warmed KRBB containing test substances, vehicle or insulin in the appropriate wells, and incubation was continued at 37° C. for 20 min. During the incubation, a mixture of 10×2-deoxyglucose was prepared as follows: 985 µl KRBB, 10 µl 10 mM 2-deoxyglucose, 5 µl [$^3$H]-2-deoxyglucose (1 mCi/ml). At the end of the 20 min incubation period, 30 µl of the 10× 2-deoxyglucose mixture was added to all wells and incubated at 37° C. for a further 10 min. The buffer solution was removed from wells and the cells were washed three times with 1 ml ice-cold KRBB. 100 µl of 0.5 N NaOH was added to all wells and incubated at room temperature for 30 min. 50 µl of the resulting cell lysate was transferred to a white 96 well plate. 200 µl Microscint 20 was added to all wells, covered with a topseal, and shaken at room temperature for 30 min. Quantitation of [$^3$H]-2-deoxyglucose content was determined for each well by scintillation counting.

Figure 4:
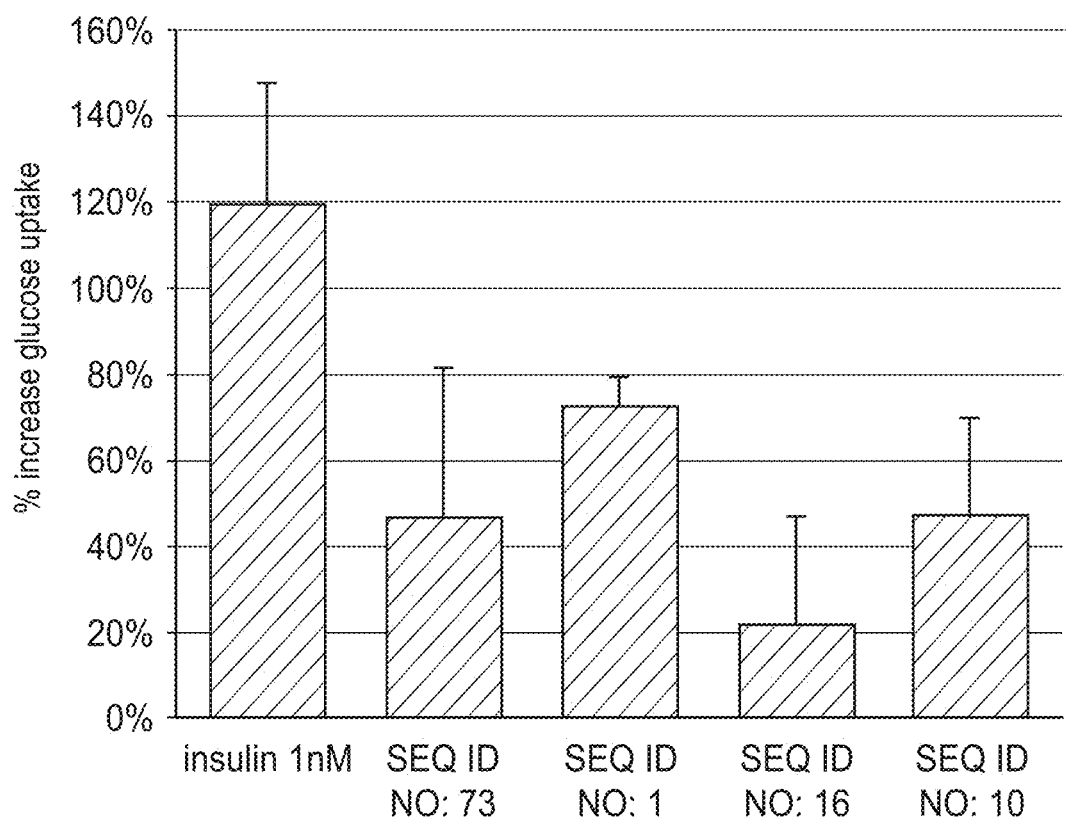
FIG. 4 shows a graph illustrating increased glucose uptake by fully differentiated 3T3 adipocytes treated with HBD1 fragments according to some embodiments of the present technology. The cells were exposed to the test compounds at a concentration of 3 µg/ml for 24 hours before testing for [$^3$H]-2-deoxyglucose uptake. All tested HBD1 peptides stimulated increased glucose uptake by the 3T3-LI adipocytes.

The following HBD1 peptides: SEQ ID NO: 1 (KHHL-GLEEPKKLR), SEQ ID NO: 10 (HLGLEEPKK), SEQ ID NO: 16 (HHLGLEEPKK), and SEQ ID NO: 73 (C18:0-HLGLEEPKK), were tested in the described assay to determine the effect on glucose uptake by the 3T3-LI adipocytes. Results of HBD1 peptide incubation on glucose uptake by the differentiated 3T3-LI adiopocytes are presented in FIG. 4. In summary, all tested HBD1 peptides stimulated increased glucose uptake by the 3T3-LI adipocytes.

Example 4: Demonstration of the Effect of the HBD1 Peptides on Glucose Uptake by Skeletal Muscle Cells In Vitro, and Demonstration that the HBD1 Peptides Utilize the Same Receptor and Mechanisms as IGFBP2 to Increase Glucose Uptake Previous studies have demonstrated that insulin-like growth factor 2 (IGFBP2) acts through the cell surface receptor, Receptor-Type Protein Tyrosine Phosphatase-β (RPTPβ) to activate both the Akt and the AMPK pathways to increase glucose uptake (Assefa et al. 2017). The following studies were undertaken to determine if the HBD1 peptides utilized the same receptor and transduction pathways to increase glucose uptake. The studies were performed using cultured, fully differentiated C2C12 mouse skeletal muscle myotubes. The cells were prepared by growing C2C12 cells to confluent density in DMEM with 25 mM glucose and 10% fetal bovine serum in 24 well plates. At this time, the medium was changed to differentiation medium (DMEM with 25 mM glucose and 2% horse serum) for 6 days with medium changed every third day. The various treatments were diluted in serum-free medium and, after washing the cells with serum-free medium, were added to the cells and incubated for 2 hours or alternative times, depending on the treatment. At the end of incubation period, the media was removed and 1.0 ml of glucose-free Krebs ringer bicarbonate buffer (pH 7.4), containing the same treatments, was added and incubation continued for 10 minutes. At the end of the 10 min incubation period, $^3$H-2-deoxyglucose (0.5 mCi/well) (specific activity=8 Ci/mmole) was added directly to all wells, and the incubation continued for an additional 10 mM. The wells were then rinsed three times with ice cold phosphate buffered saline, the cells were extracted with 0.5 N NaOH, and the $^3$H-2-deoxyglucose content of the cell lysate quantitated by scintillation counting.

For signaling studies the cells were prepared the same way except 6-well plates were used. After 6 days incubation in differentiating medium, the cells were washed with serum-free medium. The various treatments were then added in serum free medium containing 0.1% BSA. HBD1 peptides were added and incubated for 8 hours. When utilizing IGF-I, incubation was for 15 minutes after IGF-1 addition. Following incubation the cells were lysed in RIPA buffer and sonicated. The cell lysate was centrifuged and the supernatant analyzed for either Akt or AMPK by SDS PAGE using a 10% gel followed by immunoblotting with the appropriate antibody.

Figure 5A:
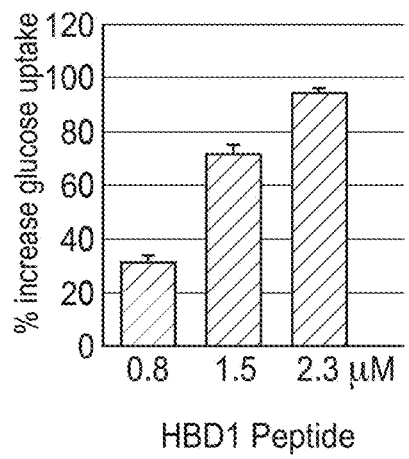
FIGS. 5A-5C show graphs illustrating both dose-dependent (FIG. 5A) and time-dependent (FIG. 5B) increases in glucose uptake by fully differentiated C2C12 mouse skeletal muscle myotubes when treated with HBD1 fragments according to some embodiments of the present technology. In particular: HBD1 SEQ ID NO: 73 (C18:0-HLGLEEPKK) at 0.8 µM, 1.5 µM, and 2.3 µM; or 1.5 µM SEQ ID NO: 73 (C18:0-HLGLEEPKK) for 2, 4, and 16 hours prior to testing glucose uptake. Further, addition of HBD1 peptide SEQ ID NO: 73 (C18:0-HLGLEEPKK) in combination with insulin produced an additive increase in glucose uptake (FIG. 5C).
Figure 5B:
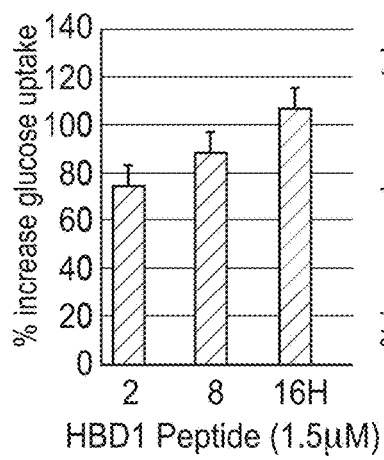
Figure 5C:
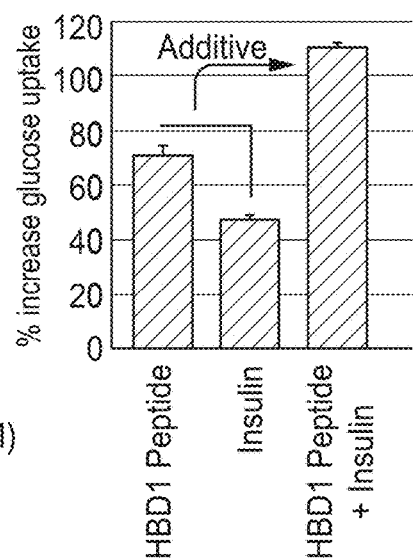

When tested for ability to increase glucose uptake by fully differentiated C2C12 mouse skeletal muscle myotubes, HBD1 peptide SEQ ID NO: 73 (C18:0-HLGLEEPKK), stimulated increased glucose uptake as compared with vehicle-treated controls in both a dose- and time-dependent manner (FIGS. 5A-5B). Further, addition of HBD1 peptide SEQ ID NO: 73 (C18:0-HLGLEEPKK) in combination with insulin produced an additive increase in glucose uptake (FIG. 5C).

Figure 6:
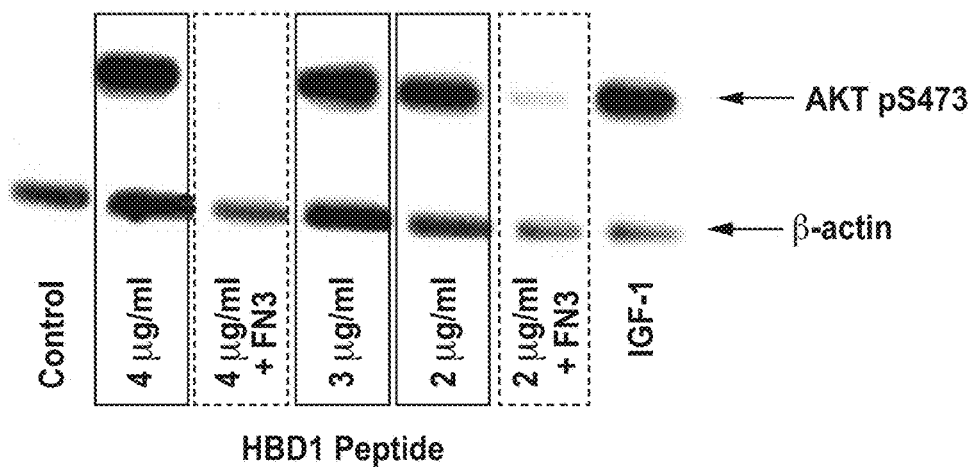
FIG. 6 shows a graph illustrating dose-dependent phosphorylation (activation) of the Akt pathway by fully differentiated C2C12 mouse skeletal muscle myotubes when treated with a HBD1 fragment according to an embodiment of the present technology. In particular: HBD1 SEQ ID NO: 73 (C18:0-HLGLEEPKK). The Akt pathway is utilized by both insulin and IGF1 to ultimately induce GLUT4 translocation to the cell membrane to facilitate the uptake and metabolism of glucose. The activation of Akt by HBD1 peptide SEQ ID NO: 73 (C18:0-HLGLEEPKK) was prevented by treatment with anti-fibronectin antibodies, which have been previously demonstrated to prevent binding of IGFBP2 to the RPTPβ receptor and activation of the Akt pathway.

To examine the intracellular transduction pathways utilized by the HBD1 peptides, following treatment with HBD1 peptide SEQ ID NO: 73 (C18:0-HLGLEEPKK), cell lysate proteins were separated by SDS PAGE and immunoblotted with anti-Akt pS473 antibodies. It was observed that HBD1 peptide SEQ ID NO: 73 (C18:0-HLGLEEPKK) induced a dose-related increase in phosphorylated Akt (FIG. 6). The detection of phosphorylated Akt was completely abolished by treatment with anti-fibronectin antibodies (FN3), which have been demonstrated to prevent interaction with the RPTPβ receptor, and which has previously been demonstrated to block IGFBP2 interaction with RPTPβ (Shen et al. 2012).

Figure 7:
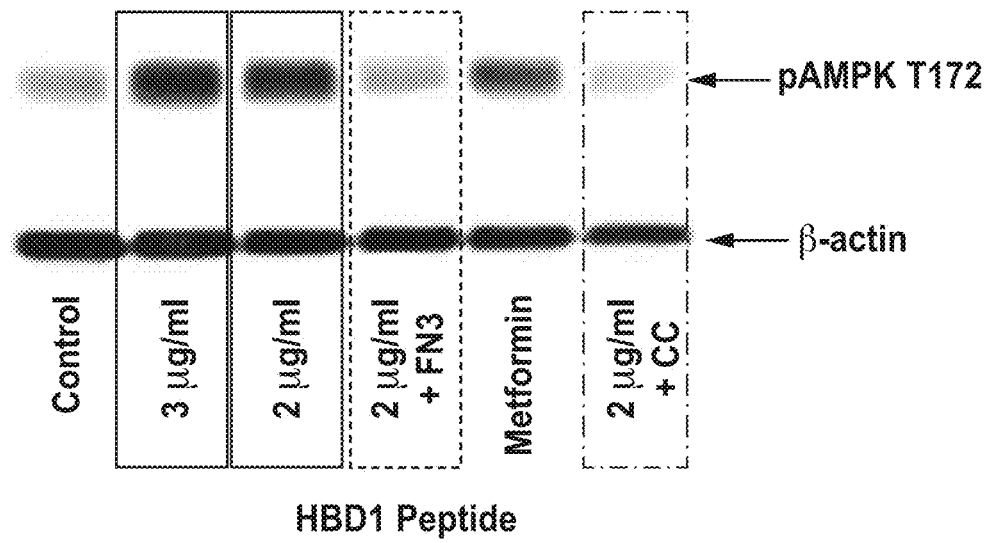
FIG. 7 shows a graph illustrating dose-dependent phosphorylation (activation) of the AMPK pathway by fully differentiated C2C12 mouse skeletal muscle myotubes when treated with a HBD1 fragment according to one embodiment of the present technology. In particular: HBD1 SEQ ID NO: 73 (C18:0-HLGLEEPKK). The AMPK pathway is both insulin and IGF1 independent, but acts ultimately to induce GLUT4 translocation to the cell membrane to facilitate the uptake and metabolism of glucose. The activation of AMPK by HBD1 peptide SEQ ID NO: 73 (C18:0-HLGLEEPKK) was prevented by both treatment with anti-fibronectin antibodies, which have been previously demonstrated to prevent binding of IGFBP2 to the RPTPβ receptor and activation of the Akt pathway, and treatment with the AMPK-specific inhibitor, Compound C (CC).

To examine further the intracellular transduction pathways utilized by the HBD1 peptides, following treatment with HBD1 peptide SEQ ID NO: 73 (C18:0-HLGLEEPKK), cell lysate proteins, were separated by SDS PAGE and immunoblotted with anti-pAMPK T172. It was observed that treatment with HBD1 peptide SEQ ID NO: 73 (C18:0-HLGLEEPKK) resulted in a dose-dependent increase in phosphorylated AMPK (FIG. 7). The detection of phosphorylated AMPK was completely abolished by treatment with either anti-fibronectin antibodies (FN3), which have been demonstrated to prevent interaction with the RPTPβ receptor, and which have previously been demonstrated to block IGFBP2 interaction with RPTPβ (Shen et al. 2012), or with Compound C, a specific inhibitor of AMPK activation, and which has also previously been demonstrated to block IGFBP2-stimulated glucose uptake in cultured adipocytes (Assefa et al. 2017).

Figure 8:
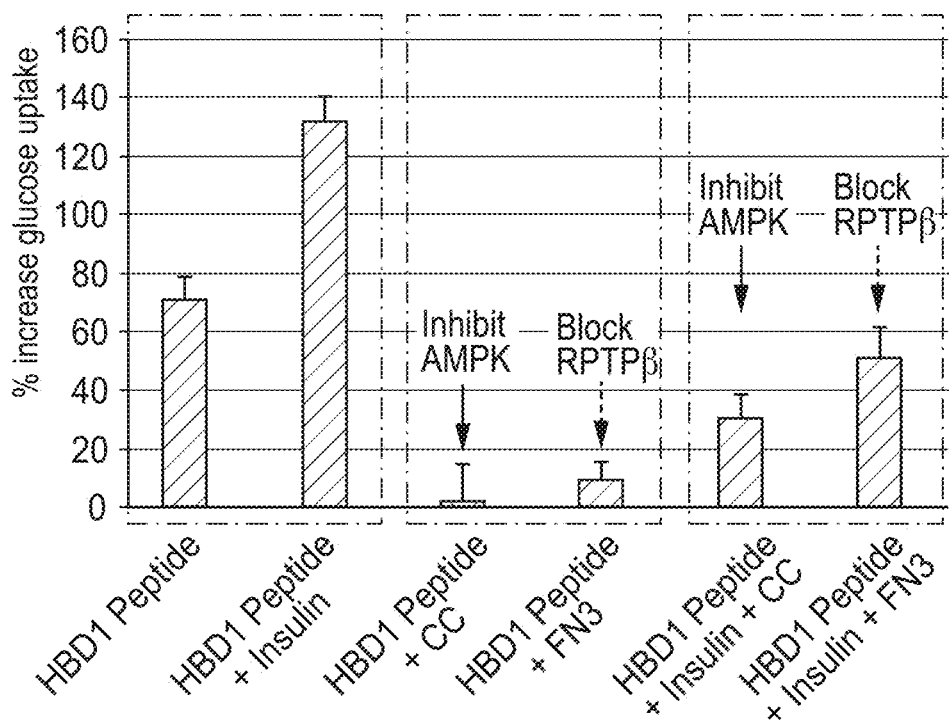
FIG. 8 shows a graph illustrating increased glucose uptake by fully differentiated C2C12 mouse skeletal muscle myotubes when treated with a HBD1 fragment according to one embodiment of the present technology. In particular: 1.5 µM of SEQ ID NO: 73 (C18:0-HLGLEEPKK), both alone and in an additive manner with insulin. The increased uptake of glucose by HBD1 peptide SEQ ID NO: 73 (C18:0-HLGLEEPKK) was prevented by both treatment with anti-fibronectin antibodies, which have been previously demonstrated to prevent binding of IGFBP2 to the RPTPβ receptor, and treatment with the AMPK-specific inhibitor, Compound C (CC).

In a separate experiment, treatment with HBD1 peptide SEQ ID NO: 73 (C18:0-HLGLEEPKK), was once again demonstrated to increase glucose uptake by fully differentiated mouse skeletal muscle myotubes, as well as to act additively with insulin (FIG. 8). In keeping with the effects observed on the intracellular transduction pathways, treatment with either anti-fibronectin antibodies (FN3), which have been demonstrated to prevent interaction with the RPTPβ receptor, and which have previously been demonstrated to block IGFBP2 interaction with RPTPβ (Shen et al. 2012), or with Compound C, a specific inhibitor of AMPK activation, and which has also previously been demonstrated to block IGFBP2-stimulated glucose uptake in cultured adipocytes (Assefa et al. 2017), completely abolished the ability of HBD1 peptide SEQ ID NO: 73 (C18:0-HLGLEEPKK) to increase glucose uptake, either alone or when added together with insulin.

Overall, the data presented herein establish the potential of HBD1, HBD1 fragments and analogs thereof in modulating glucose metabolism, insulin metabolism as well as leptin metabolism. The mechanism of action of HBD1 on osteoblast differentiation and on glucose uptake is similar, in that they share the same receptor (RPTPbeta) and the same intracellular pathways (Akt). Therefore it can be envisioned that the HBD1 analogs that have shown potency in osteoblast differentiation (as per osteoblast differentiation assays previously reported in, for example, WO 2018/145006) will also be effective on glucose metabolism.

It is understood that the data reported in the present specification are only given to illustrate the present disclosure and may not be regarded as constituting a limitation thereof.

While the present disclosure has been described in connection with specific embodiments thereof, it will be understood that it is capable of further modifications and this application is intended to cover any variations, uses, or adaptations of the present disclosure following, in general, the principles of the present disclosure and including such departures from the present disclosure as come within known or customary practice within the art to which the present disclosure pertains and as may be applied to the essential features hereinbefore set forth, and as follows in the scope of the appended claims.

INCORPORATION BY REFERENCE

All references cited in this specification, and their references, are incorporated by reference herein in their entirety where appropriate for teachings of additional or alternative details, features, and/or technical background.

EQUIVALENTS

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following embodiments.

BIBLIOGRAPHY

WO 005/014635;
U.S. Pat. No. 9,220,746;
PCT/US2018/16869
Xi G. et al. The Heparin-Binding Domains of IGFBP-2 Mediate Its Inhibitory Effect on Preadipocyte Differentiation and Fat Development in Male Mice. *Endocrinology,* 154(11):4146-4157 (2013).
Poster 0268 by Xi et al. presented at the Annual Meeting of the American Society for Bone and Mineral Research (ASBMR) in Atlanta on Sep. 16-19, 2016. A unique peptide containing the heparin binding domain of IGFBP-2 increases bone mass in ovariectomized (OVX) rats.
Wheatcroft S B, Kearney M T, Shah A M, Ezzat V A, Miell J R, Modo M, Williams S C, Cawthorn W P, Medina-Gomez G, Vidal-Puig A, Sethi J K, Crossey P A. IGF-binding protein-2 protects against the development of obesity and insulin resistance. Diabetes. 2007; 56(2): 285-294.
DeMambro V E, Clemmons D R, Horton L G, et al. Gender-specific changes in bone turnover and skeletal architecture in igfbp-2-null mice. Endocrinology. 2008; 149(5):2051-2061.
Hedbacker K, Birsoy K, Wysocki R W, et al. Antidiabetic effects of IGFBP2, a leptin-regulated gene. Cell Metab. 2010; 11 (1): 11-22.
Xi, G. et al. (2014) IGFBP-2 directly stimulates osteoblast differentiation. J. Bone Miner. Res. 20, 2427-2438
Kawai M, Breggia A C, DeMambro V E, et al. The heparin binding domain of IGFBP-2 has insulin-like growth factor binding-independent biologic activity in the growing skeleton. J Biol Chem. 2011; 286(16): 14670-80.

Shen X, Xi G, Maile L A, et al. Insulin-like growth factor (IGF) binding protein 2 functions coordinately with receptor protein tyrosine phosphatase B and the IGF-I receptor to regulate IGF-I-stimulated signaling. Mol Cell Biol. 2012; 32(20):4116-30.

Assefa B, Mahmoud A M, Pfeiffer A F H, et al. Insulin-Like Growth Factor (IGF) Binding Protein-2, Independently of IGF-1, Induces GLUT-4 Translocation and Glucose Uptake in 3T3-L1 Adipocytes. Oxid Med Cell Longev. 2017; 2017:3035184.

The invention claimed is:

1. A method for treatment of a disorder associated with at least one of impaired glucose metabolism, impaired insulin metabolism, and impaired leptin metabolism in a subject, the method comprising: administering to a subject in need thereof a therapeutically effective amount of
   i) a peptide consisting of a fragment of heparin binding domain 1 (HBD1) as set forth in SEQ ID NO: 1, the fragment being 6 to 10 amino acids in length;
   ii) an analog of a peptide set forth in i), the analog being 6 to 8 amino acids in length and different in sequence from the peptide set forth in i) by 1 or 2 amino acid substitutions, wherein the substitutions are to alanine or are a conservative substitution;
   iii) an analog of a peptide set forth in i), the analog being 9 or 10 amino acid in length and different in sequence from the peptide set forth in i) by 1, 2 or 3 amino acid substitutions, wherein the substitutions are to alanine or are a conservative substitution; or
   iv) a pharmaceutically acceptable salt of any one of the peptides set forth in i), ii) and iii).

2. The method according to claim 1, wherein the disorder is a rare genetic obesity disorder.

3. The method according to claim 1, wherein the disorder is syndromic obesity.

4. The method according to claim 1, wherein the disorder is a disorder associated with leptin receptor (LEPR) deficiency or with leptin deficiency.

5. The method according to claim 1, wherein the disorder is one or more of: hypoglycemia, hyperglycemia, carbohydrate intolerance, glucose intolerance, impaired fasting glucose, impaired glucose tolerance, carbohydrate-lipid metabolism disturbance, hyperinsulinemia, Type IV hyperlipoproteinemia, insulin resistance, diabetes Type I, diabetes Type II, acromegaly, a disorder associated with leptin receptor (LEPR) deficiency, a disorder associated with LEPR mutations, leptin receptor-related monogenic obesity, and syndrome of extreme insulin resistance.

6. The method according to claim 1, wherein the peptide is pegylated.

7. The method according to claim 1, wherein the peptide is acylated.

8. The method according to claim 1, wherein the peptide is cyclic.

9. The method according to claim 1, wherein the amino acid substitutions are conservative substitutions.

10. The method according to claim 1, wherein the peptide is as set forth in SEQ ID NO: 73.

11. The method according to claim 1, wherein the peptide is SEQ ID NO: 7, SEQ ID NO: 8, SEQ ID NO: 10, SEQ ID NO: 11, SEQ ID NO: 12, SEQ ID NO:13, SEQ ID NO: 14, SEQ ID NO: 17, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 106, SEQ ID NO: 107, SEQ ID NO: 108, SEQ ID NO: 109, SEQ ID NO: 110, SEQ ID NO: 111, SEQ ID NO: 112, or SEQ ID NO: 113.

12. The method according to claim 1, wherein said administration is intrathecal, subcutaneous, cutaneous, oral, intravenous, intranasal, intraperitoneal, intramuscular, via an implant, via a matrix, via a gel, or any combination thereof.

13. The method according to claim 1, wherein the therapeutically effective amount is from about 0.01 µg/kg to about 100 mg/kg.

14. The method according to claim 1, wherein the therapeutically effective amount is from about 0.3 mg/kg to about 3 mg/kg.

15. The method according to claim 1, wherein said administering is performed once, twice or three times daily.

16. The method of claim 1, wherein the fragment is 6 to 9 amino acids in length and the analog is 6 to 9 amino acid in length.

* * * * *